(12) United States Patent
Yamazaki

(10) Patent No.: US 8,212,892 B2
(45) Date of Patent: Jul. 3, 2012

(54) IMAGE PICKUP APPARATUS

(75) Inventor: Kenji Yamazaki, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 12/880,529

(22) Filed: Sep. 13, 2010

(65) Prior Publication Data
US 2011/0069199 A1    Mar. 24, 2011

Related U.S. Application Data

(63) Continuation of application No. PCT/JP2010/057871, filed on May 10, 2010.

(30) Foreign Application Priority Data

May 14, 2009    (JP) ................................. 2009-117797

(51) Int. Cl.
H04N 5/235 (2006.01)

(52) U.S. Cl. .................................................. 348/229.1

(58) Field of Classification Search ............... 348/229.1, 348/620, 70, 326, 745; 600/476, 181, 109, 600/921, 160; 382/151
See application file for complete search history.

(56) References Cited

U.S. PATENT DOCUMENTS

| | | | |
|---|---|---|---|
| 5,667,474 A * | 9/1997 | Nishimura | 600/109 |
| 7,043,291 B2 | 5/2006 | Sendai | |
| 7,383,994 B2 * | 6/2008 | Smith | 235/462.01 |
| 2003/0118106 A1 * | 6/2003 | Kondo et al. | 375/240.16 |
| 2006/0058684 A1 * | 3/2006 | Sendai | 600/476 |
| 2009/0021578 A1 * | 1/2009 | Yamazaki et al. | 348/65 |

FOREIGN PATENT DOCUMENTS

| | | |
|---|---|---|
| EP | 1 256 310 A2 | 11/2002 |
| JP | 01-181840 | 7/1989 |
| JP | 01-250918 | 10/1989 |
| JP | 04-253829 | 9/1992 |
| JP | 04-296191 | 10/1992 |
| JP | 07-246184 | 9/1995 |
| JP | 07-275198 | 10/1995 |
| JP | 8-0111812 | 4/1996 |
| JP | 09-138356 | 5/1997 |
| JP | 11-234662 | 8/1999 |
| JP | 2000-209489 | 7/2000 |

(Continued)

OTHER PUBLICATIONS

Japanese Office Action dated Nov. 2, 2010 together with an English language translation issued in JP2010-535154.

(Continued)

*Primary Examiner* — Tuan Ho
*Assistant Examiner* — Akshay Trehan
(74) *Attorney, Agent, or Firm* — Scully, Scott, Murphy & Presser, P.C.

(57) ABSTRACT

An image pickup apparatus includes a light source section that can radiate light of the same wavelength onto the same region of a subject twice within a one-frame period making up one image, a brightness detection section that detects brightness of two returning light images when light has been radiated twice, and a synthetic image generation section that generates a synthetic image obtained by synthesizing the two returning light images using the light of the same wavelength and under the same exposure quantity based on the detection result of the brightness.

18 Claims, 22 Drawing Sheets

FOREIGN PATENT DOCUMENTS

| | | |
|---|---|---|
| JP | 2001-148862 | 5/2001 |
| JP | 2002-143081 | 5/2002 |
| JP | 2002-345734 | 12/2002 |
| JP | 2003-024268 | 1/2003 |
| JP | 2003-070721 | 3/2003 |
| JP | 2005-160590 | 6/2005 |
| JP | 2005-211231 | 8/2005 |
| JP | 2005-261974 | 9/2005 |
| JP | 2006-314629 | 11/2006 |
| JP | 2007-312832 | 12/2007 |

OTHER PUBLICATIONS

Japanese Office Action dated Feb. 8, 2011 together with an English language translation issued in JP2010-535154.
International Search Report dated Jul. 6, 2010.

* cited by examiner

NORMAL OBSERVATION MODE

IMAGE PICKUP APPARATUS

CROSS REFERENCE TO RELATED APPLICATION

This application is a continuation application of PCT/JP2010/057871 filed on May 10, 2010 and claims benefit of Japanese Application No. 2009-117797 filed in Japan on May 14, 2009, the entire contents of which are incorporated herein by this reference.

BACKGROUND OF THE INVENTION

1. Field of the Invention

The present invention relates to an image pickup apparatus that radiates light onto a target region a plurality of times and generates a synthetic image from picked-up images of returning light thereof.

2. Description of the Related Art

In recent years, endoscopes are widely used which radiate illumination light onto a region to be observed or a region subject to image pickup from an illumination window provided at a distal end of an insertion portion and picks up an image thereof using an image pickup device provided on an observation window.

A light source section of an image pickup apparatus such as an endoscope apparatus using such an endoscope is provided with a light quantity adjusting section that adjusts an illumination light quantity of illumination light such as a diaphragm so as to pick up an image of a region subject to image pickup in a subject in a bright condition.

However, when an image of a distant region in the body cavity is picked up or an attempt is made to acquire an easy-to-observe image using illumination light of a narrow band wavelength, the illumination light quantity may be insufficient even if the diaphragm is fully opened.

For example, a first related art of Japanese Patent Application Laid-Open Publication No. 2006-314629 discloses that a spectral signal corresponding to a narrow band image acquired in the case of narrow band illumination light is generated through image processing by radiating light beams of overlapping wavelength bands a plurality of times.

On the other hand, a second related art of Japanese Patent Application Laid-Open Publication No. 11-234662 considerably changes an image pickup time (that is, shutter time) by an image pickup device between a first field and a second field, that is, changes an exposure quantity during radiation with illumination light (white color light) from a light source device and picks up images twice.

To be more specific, the image pickup device picks up images at 1/60 s for the first field and 1/240 s, which is a shutter time 1/4 of 1/60 s, for the second field.

By assigning weights to and adding up the two images picked up with different shutter times, the image pickup device suppresses halation using the image picked up with the longer shutter time and the image picked up with the shorter shutter time, and generates an image of a wide dynamic range.

This related art picks up images twice while keeping open the diaphragm of the light source device and acquires an image with an enlarged dynamic range.

SUMMARY OF THE INVENTION

An image pickup apparatus according to an embodiment of the present invention includes a light source section that can radiate at least two light beams of the same wavelength onto the same region of a subject within a one-frame period making up one image, a brightness detection section that detects brightness of two returning light images based on the radiation of the at least two light beams of the same wavelength, and a synthetic image generation section that generates a synthetic image obtained by synthesizing the two returning light images using the light beams of the same wavelength and under substantially the same exposure quantity based on the detection result of the brightness detection section.

An image pickup apparatus according to another embodiment of the present invention includes a light source section that can radiate at least two light beams of the same wavelength onto the same region of a subject within a one-frame period making up one image, a light quantity adjusting section provided in the light source section for adjusting a light quantity from the light source, a brightness detection section that detects brightness of two returning light images based on the radiation of the at least two light beams of the same wavelength, and a synthetic image generation section that generates a synthetic image obtained by synthesizing the two returning light images using the light beams of the same wavelength and under substantially the same exposure quantity based on the adjustment result of the light quantity adjusting section and the detection result of the brightness detection section.

DETAILED DESCRIPTION OF THE PREFERRED EMBODIMENTS

Hereinafter, embodiments of the present invention will be described with reference to the accompanying drawings.

First Embodiment

Figure 1:
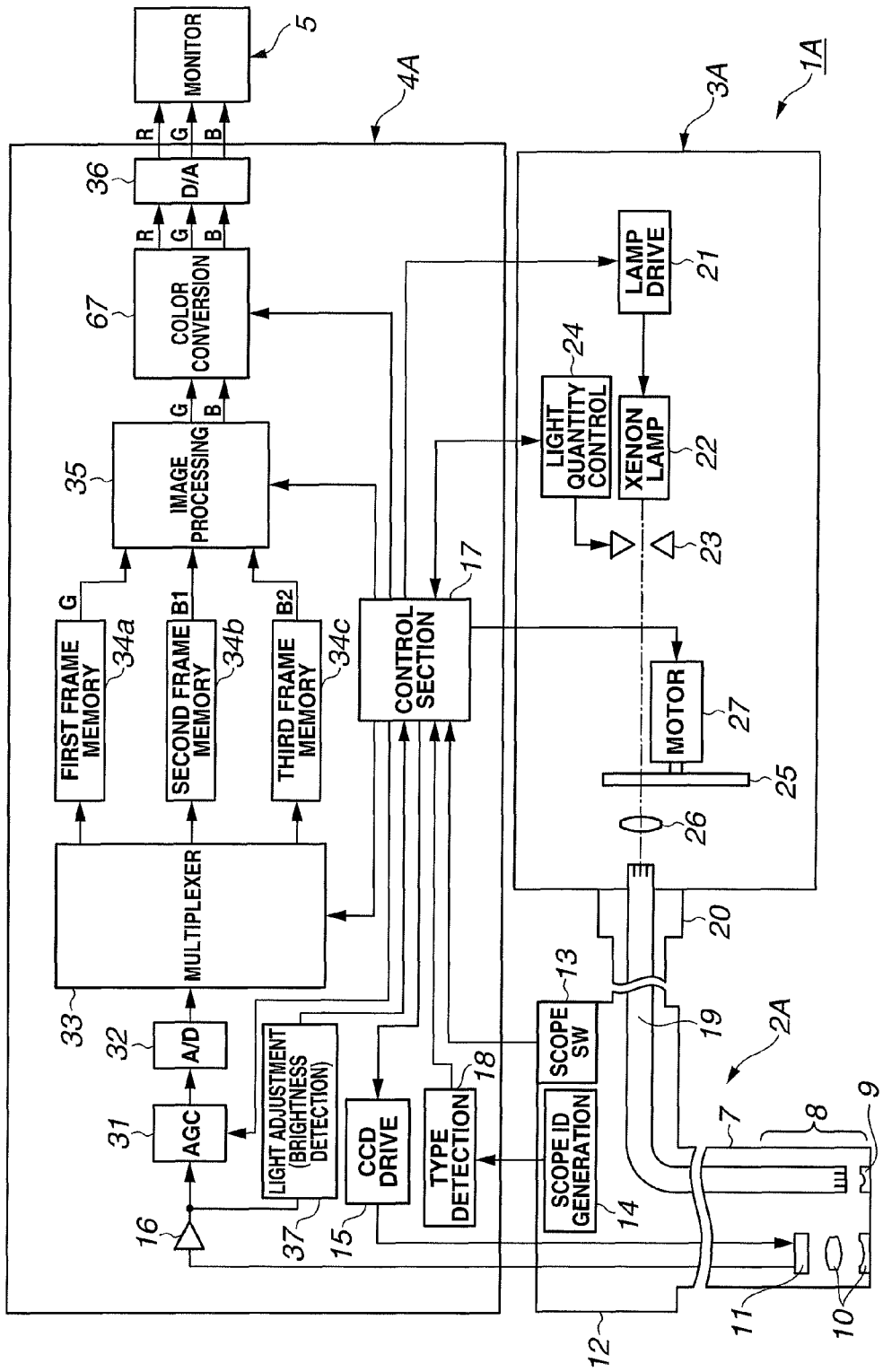
FIG. 1 is a diagram illustrating an overall configuration of an endoscope apparatus according to a first embodiment of the present invention.
Figure 2:
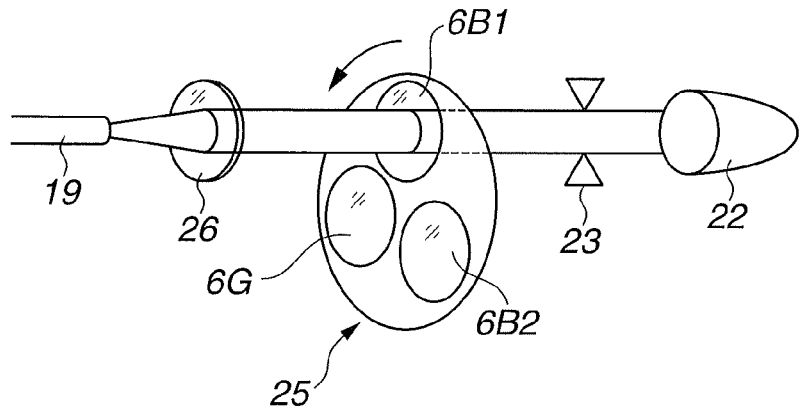
FIG. 2 is a diagram illustrating a configuration of a revolving filter peripheral section.
Figure 3A:
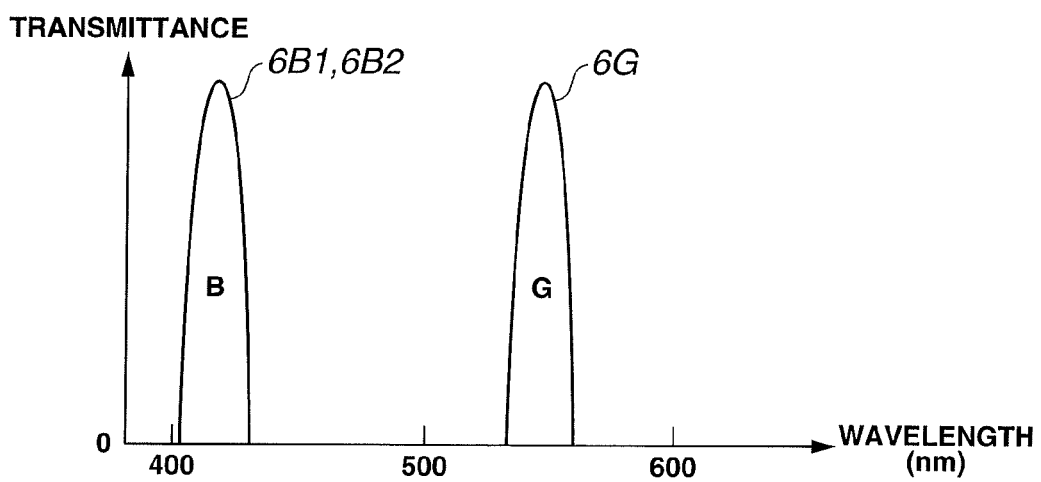
FIG. 3A is a diagram illustrating transmission characteristics of a narrow band filter provided in the revolving filter.
Figure 3B:
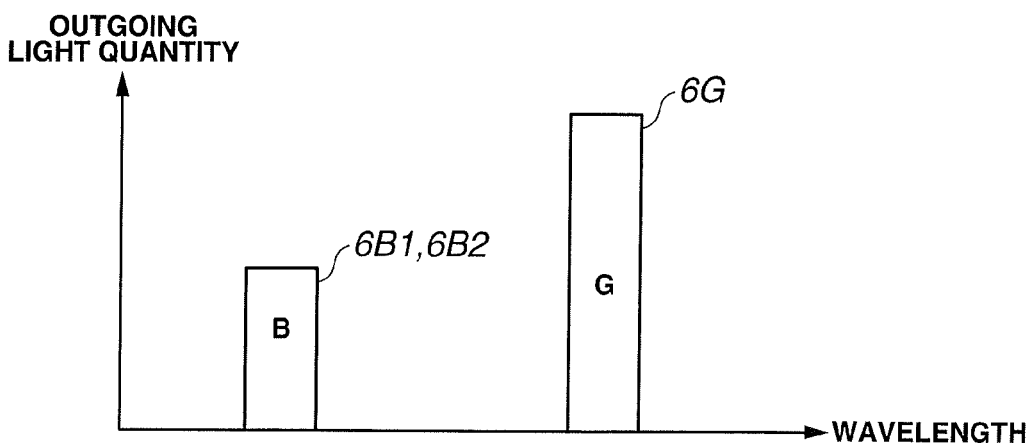
FIG. 3B is a diagram illustrating an outgoing light quantity emitted from a distal end portion of the endoscope.
Figure 4:
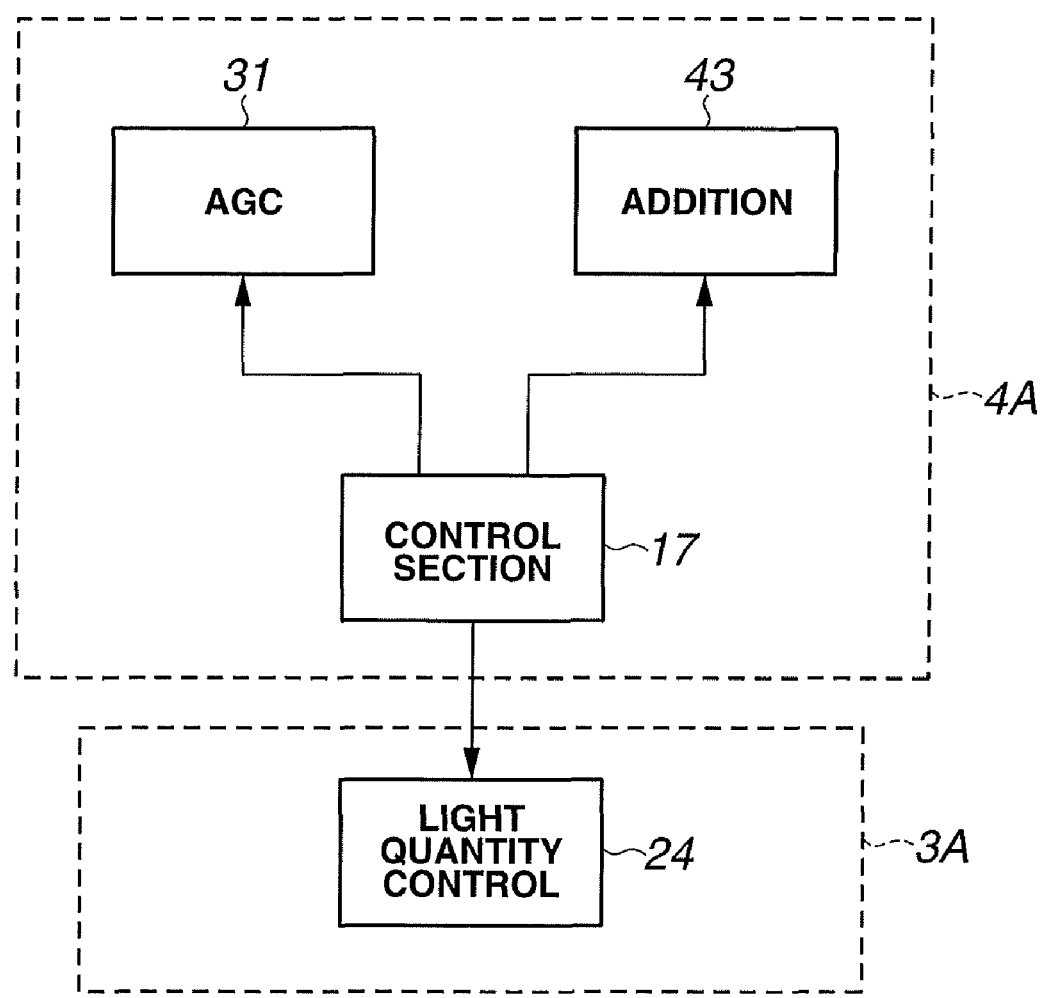
FIG. 4 is a block diagram illustrating main parts of image generating means for generating an endoscope image under the control of a control section.

FIG. 1 to FIG. 9 are related to a first embodiment of the present invention, FIG. 1 illustrates an overall configuration of an endoscope apparatus that picks up an image using narrow band light as the first embodiment of an image pickup apparatus of the present invention, FIG. 2 illustrates a schematic configuration including a revolving filter section of a light source section, FIG. 3A illustrates transmission characteristics of a narrow band filter provided in the revolving filter, FIG. 3B illustrates an outgoing light quantity, FIG. 4 illustrates main parts of image generating means for generating an endoscope image under the control of a control section.

Figure 5:
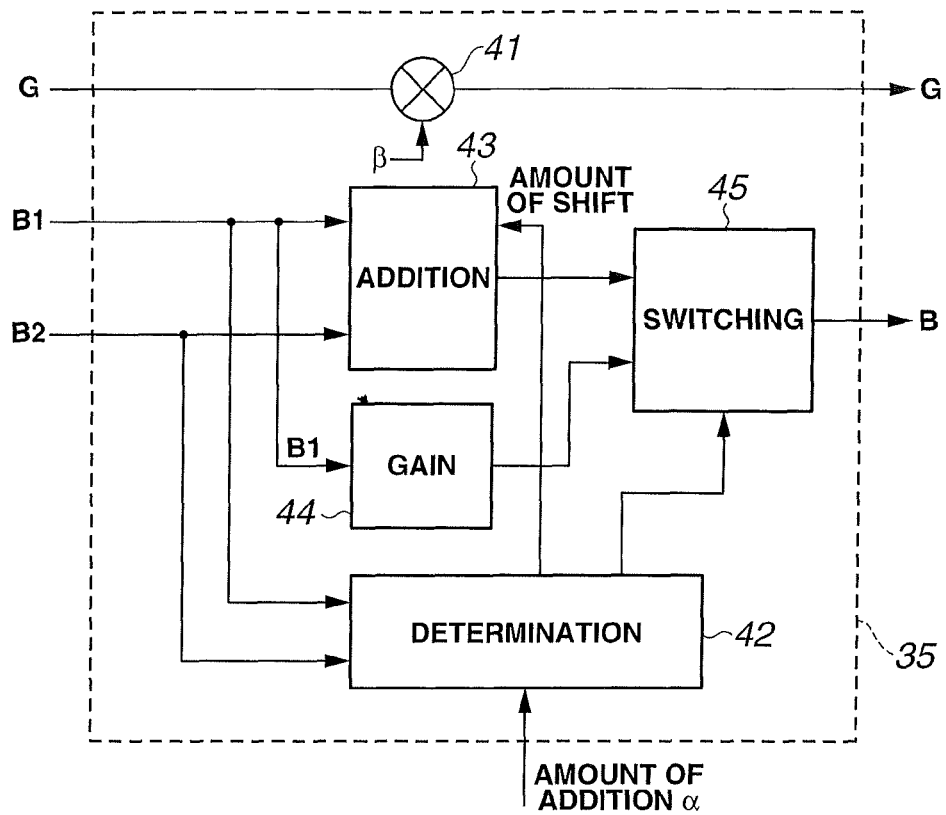
FIG. 5 is a block diagram illustrating a configuration of an image processing circuit.
Figure 6:
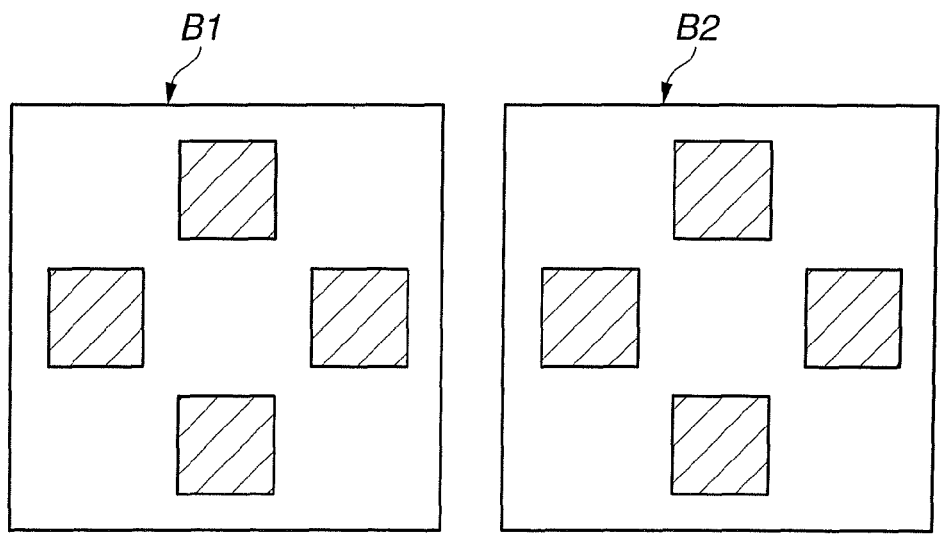
FIG. 6 is a diagram illustrating an example of local regions set to determine a normalized cross-correlation.
Figure 7:
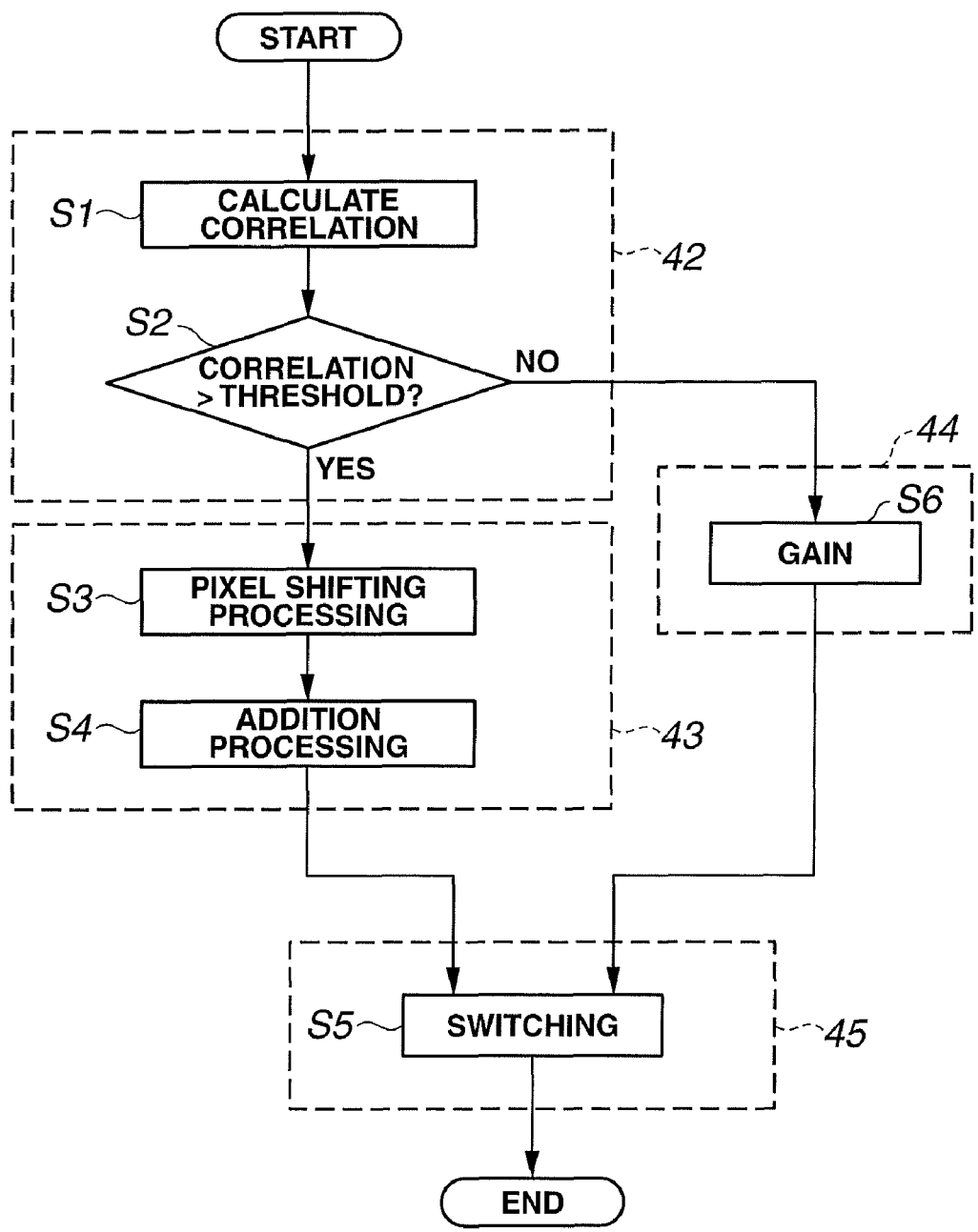
FIG. 7 is a flowchart illustrating operation contents of the respective sections of the image processing circuit.
Figure 8:
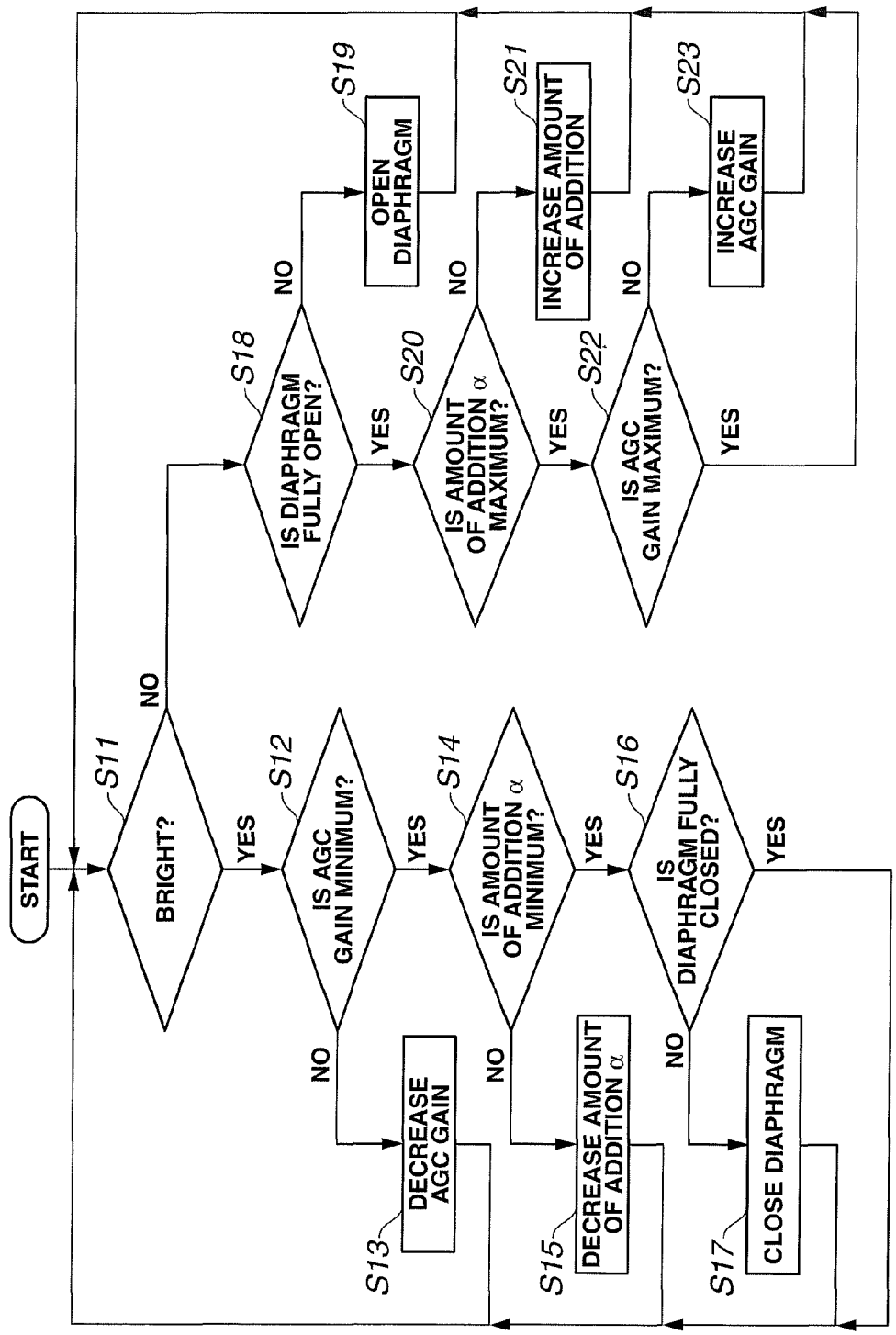
FIG. 8 is a flowchart illustrating operation contents of brightness adjustment according to the first embodiment.
Figure 9:
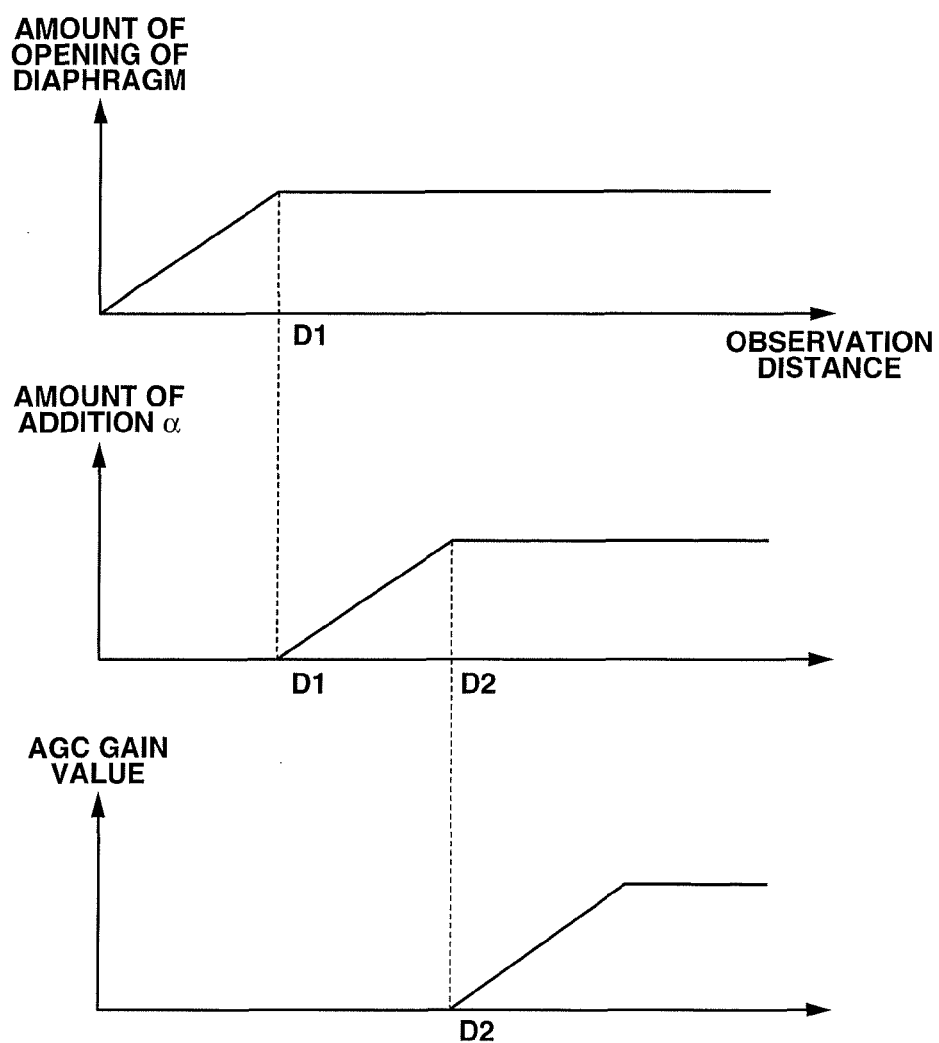
FIG. 9 is a diagram illustrating a situation in which brightness with respect to a target value of an image is adjusted with an amount of opening of the diaphragm according to the observation distance.

FIG. 5 illustrates a configuration of an image processing circuit, FIG. 6 illustrates an example of local regions set to determine a normalized cross-correlation, FIG. 7 illustrates operation contents of the respective sections of the image processing circuit, FIG. 8 illustrates operation contents of brightness adjustment according to the first embodiment and FIG. 9 illustrates a situation in which brightness with respect to a target value is adjusted according to the observation distance.

As shown in FIG. 1, an endoscope apparatus 1A making up the image pickup apparatus of the present embodiment is provided with an endoscope 2A for observing the interior of a living body as a subject, a light source section 3A that radiates narrow band illumination light for observing the interior of the living body, a processor 4A as signal processing means for performing signal processing on an image pickup signal picked up under narrow band illumination light, and a monitor 5 that displays the narrow band image generated by the processor 4A in color.

The endoscope 2A has a flexible insertion portion 7 having the order of outer diameter that allows it to be inserted in the body cavity and a distal end portion 8 provided at a distal end of the insertion portion 7 is provided with an illumination lens 9 that spreads light supplied from the light source section 3A and radiates the light onto the subject, an objective lens 10 for forming an optical image of the subject from returning light from the subject and a CCD (charge coupled device) 11 as an image pickup device disposed at an image forming position thereof.

Furthermore, an operation portion 12 provided at a rear end of the insertion portion 7 is provided with a scope switch 13 and a scope ID generation section 14 storing at least specific ID information including the type of the endoscope 2A.

The CCD 11 that forms image pickup means is driven by a CCD drive signal outputted from a CCD drive circuit 15 provided in the processor 4A, picks up an image of the subject, converts the picked-up image of the subject to an image signal and outputs the image signal to a preamplifier 16 provided on the processor 4A.

The scope switch 13 is provided with a plurality of switches such as a release switch, which instructs recording of an image signal of an image of the subject picked up by the CCD 11 as a still image.

When the operator operates the scope switch 13, an operation signal based on the operation is outputted to a control section 17 provided on the processor 4A and the control section 17 performs control on the respective sections of the endoscope apparatus 1A based on the operation signal.

When the endoscope 2A is connected to the processor 4A, the scope ID generation section 14 outputs ID information of the connected endoscope 2A to a type detection circuit 18 provided on the processor 4A. A light guide fiber 19 made up of a quartz fiber or the like for guiding light radiated from the light source section 3A is inserted through the interior of the insertion portion 7.

One end of the light guide fiber 19 has a configuration having a light source connector 20 detachably connected to the light source section 3A and the other end of the light guide fiber 19 is disposed in the vicinity of the illumination lens 9 provided at the distal end portion 8 of the insertion portion 7.

The light source section 3A includes a lamp drive circuit 21, for example, a xenon lamp 22 which is driven by the lamp drive circuit 21 so as to emit light of a wavelength band approximate to that of white color light, and a light source diaphragm (simply referred to as "diaphragm") 23 that is provided on a radiation optical path of the xenon lamp 22 for adjusting a light quantity by restricting the quantity of light emitted from the xenon lamp 22, a light quantity control circuit (or diaphragm control circuit) 24 that controls light quantity adjustment by controlling the amount of diaphragm opening of the diaphragm 23, a revolving filter 25 provided on the optical path of the xenon lamp 22 and a condenser lens 26 that condenses the light that has passed through the revolving filter 25.

The light quantity control circuit 24 outputs information on the amount of opening of the diaphragm 23 to the control section 17 of the processor 4A, adjusts the amount of opening of the diaphragm 23 based on a control signal from the control section 17 and controls light quantity adjustment.

In the present embodiment, the diaphragm 23 forming a light quantity adjusting section that adjusts a light quantity from the xenon lamp 22 as a light source of the light source section 3 is performed using the light quantity control circuit 24, but the control section 17 may also be configured to directly control the diaphragm 23.

The revolving filter 25 is attached to a rotating shaft of a rotation motor (hereinafter simply referred to as "motor") 27 that drives the revolving filter 25 to rotate. The motor 27 is provided with an encoder (not shown) attached to the rotating shaft or the like and the encoder outputs a detection signal corresponding to a rotation drive state of the revolving filter 25 to the control section 17 of the processor 4A. The control section 17 controls the rotation of the motor 26 so that the rotation speed is kept constant.

FIG. 2 illustrates a configuration of the peripheral section of the revolving filter 25.

The revolving filter 25 is disk-shaped and provided with three openings at equal angles in its circumferential direction, and the three openings are each provided with a filter having narrow band transmission characteristics.

To be more specific, as shown in FIG. 3A, B filters 6B1 and 6B2 that allow to pass narrow band wavelengths of blue (B) and a G filter 6G that allows to pass a narrow band wavelength of green (G) are attached. As shown in FIG. 3A, the B filters 6B1 and 6B2 have characteristics of allowing to pass, for example, light of a narrow band of 400 to 430 nm centered on 415 nm and the G filter 6G has characteristics of allowing to pass, for example, light of a narrow band of 530 to 550 nm centered on 540 nm.

Furthermore, as shown in FIG. 3A, integral values of transmittance of the B filters 6B1 and 6B2 and the G filter 6G are set so as to have substantially the same value.

The illumination light beams of B of a narrow band that have passed through the B filters 6B1 and 6B2 have the same wavelength band, but are also expressed as B1 and B2 for convenience. Moreover, as will be described later, image pickup signals picked up under the illumination light beams of B of a narrow band that have passed through the B filters 6B1 and 6B2 are also expressed using B1 and B2.

The operation of the lamp drive circuit 21 and the amount of diaphragm opening of the diaphragm 23 are controlled by the control section 17.

The present embodiment picks up an image of the subject using the illumination light of a narrow band shown in FIG. 3A. For this reason, the illumination light quantity may tend to be lacking compared to the case of using wideband illumination light which is normally widely used.

Furthermore, when the light beams that have passed through the B filters 6B1 and 6B2 and the G filter 6G shown in FIG. 3A are transmitted through the light guide fiber 19, since transmission loss on the short wavelength B side tends to be greater according to optical transmission characteristics of the light guide fiber 19, an overview of the outgoing light quantity when emitted from the illumination window of the distal end portion 8 as illumination light is as shown, for example, in FIG. 3B.

As shown in FIG. 3B, compared to the outgoing light quantity of G, the outgoing light quantity when the B filters 6B1 and 6B2 are used is reduced to, for example, nearly half of the outgoing light quantity of G. Therefore, the illumination light quantity in the case of using the B filters 6B1 and 6B2 in particular tends to be lacking with respect to the G filter 6G.

For this reason, as shown in FIG. 2, the present embodiment uses the two filters 6B1 and 6B2 of the same transmission characteristics in the circumferential direction of the revolving filter 25, radiates light onto the same region of the subject to be observed twice (every time the revolving filter 25 makes one rotation) and picks up images twice using the returning light corresponding to the respective radiations.

The respective picked-up images are subjected to processing of generating a synthetic image, or to be more specific, an aligned image (or superimposed image) resulting from an aligned addition (or superimposed addition) of the two picked-up images by an addition circuit 43 as a synthetic image generation section in an image processing circuit 35, which will be described later. A synthetic image of high image quality with an improved S/N is thereby generated and displayed on the monitor 5.

When a synthetic image is generated in such a way, light beams of the same wavelength used to generate a synthetic image are set to the same light quantity (or intensity) from the standpoint of generating a synthetic image of a good S/N.

The processor 4A includes the CCD drive circuit 15, a preamplifier 16, the control section 17, the type detection circuit 18, an AGC (auto gain control) circuit 31, an A/D (analog/digital) conversion circuit 32, a multiplexer 33, a first frame memory 34a, a second frame memory 34b, a third frame memory 34c, the image processing circuit 35 that performs image processing on a picked-up image including an addition circuit 43 as a synthetic image generation section, a D/A (digital/analog) conversion circuit 36 and a light adjustment circuit (or brightness detection circuit) 37.

The image pickup signal outputted from the CCD 11 is amplified by the preamplifier 16 and then inputted to the AGC circuit 31 and the light adjustment circuit (or brightness detection circuit) 37 as a brightness detection section.

The light adjustment circuit 37 detects average brightness of the picked-up image from the image pickup signal amplified by the preamplifier 16.

Furthermore, the light adjustment circuit 37 compares the average brightness with a predetermined brightness target value. The light adjustment circuit 37 then adjusts the amount of opening of the diaphragm 23 using, for example, a signal corresponding to the difference from the target value as a light adjustment signal for dimming (brightness detection signal) via the control section 17 and the light quantity control circuit 24.

Furthermore, the AGC circuit 31 as an auto gain adjusting section automatically adjusts the gain of the amplification circuit therein, that is, an AGC gain so that an image pickup signal inputted has predetermined amplitude. The AGC gain operation of the AGC circuit 31 is controlled by the control section 17.

When generating a synthetic image from the two picked-up images obtained using the filters 6B1 and 6B2 having the same transmission characteristics, the present embodiment in the configuration shown in FIG. 1 forms image generating means as shown in FIG. 4.

The control section 17 in the processor 4A controls the operations of the AGC circuit 31 and the addition circuit 43 that generates a synthetic image (in the image processing circuit 35) based on the light adjustment signal, that is, brightness from the light adjustment circuit 37 and also controls the operation of light quantity control of the light quantity control circuit 24 of the light source section 3A.

The operation according to the configuration will be described later using FIG. 8. The control section 17 basically performs control so as to achieve target brightness by giving the highest priority to light quantity adjustment by the diaphragm 23.

The image pickup signal that has passed through the AGC circuit 31 is converted from an analog signal to a digital signal by the A/D conversion circuit 32.

The image pickup signal converted to the digital signal is temporarily recorded in a first frame memory 34a, a second frame memory 34b and a third frame memory 34c, which are image pickup signal recording means, via a multiplexer 33 that changes the recording destination of the image pickup signal.

The image pickup signals recorded in the first frame memory 34a, the second frame memory 34b and the third frame memory 34c are synchronized with each other at predetermined time periods, and then inputted to the image processing circuit 35 and subjected to predetermined image processing.

The image pickup signals are recorded as image pickup signals G, B1 and B2 picked up under narrow band illumination light beams of G, B1 and B2 that have passed through the G filter 6G, and the B filters 6B1 and B2 in the first frame memory 34a, the second frame memory 34b and the third frame memory 34c respectively.

In this case, the image processing circuit 35 has a configuration as shown in FIG. 5.

The image pickup signal G is multiplied, for example, $\beta$-fold by a multiplication circuit 41 under the control of the control section 17 and then outputted as an image signal G from the image processing circuit 35. The relationship of the coefficient $\beta$ with the coefficient of the following amount of addition $\alpha$ is set to $\beta=(\alpha+1)/k$. Here, k is a value (for example, 2 in FIG. 3A) set beforehand according to the ratio of the integral values on the outgoing light quantities of B and G as shown in FIG. 3B. In order to reduce individual variations in the optical systems or the like in the light source section 3A and the endoscope 2A or variations in spectral sensitivity of the CCD, the control section 17 may adjust the value k so that average brightness of image signals G' and B' outputted from the image processing circuit 35 is substantially equal when an image of a predetermined subject is picked up (and when the amount of addition $\alpha=0$).

On the other hand, the image pickup signals B1 and B2 are inputted to a determination circuit 42 and an addition circuit 43 as a synthetic image generation section making up an amount of misalignment detection section inside the image processing circuit 35 and one image pickup signal B1 which serves as a reference is further inputted to a gain circuit 44 as an alternate image generation section.

The determination circuit 42 determines a normalized cross-correlation between the image pickup signals B1 and B2 corresponding to returning light images picked up under the two narrow band illumination light beams, that is, illumination light beams of B1 and B2 as will be described below, and thereby detects an amount of misalignment between both image pickup signals B1 and B2.

Furthermore, the determination circuit 42 forms the amount of misalignment detection section that detects the amount of misalignment and also forms a determining section that determines, whether or not to generate an aligned image as a synthetic image by the addition circuit 43 from the detection result (namely, whether or not a synthetic image should be outputted).

The addition circuit 43 performs addition processing of generating an aligned image as a synthetic image on the image pickup signals B1 and B2 according to:

$$B = B1 + \alpha \cdot B2 \, (0 \leq \alpha \leq 1 : \text{real number}) \quad (1)$$

The image pickup signal B2 is an image pickup signal whose misalignment has been corrected based on the amount of shift. The addition processing of generating an aligned image as shown in Equation 1 includes cases where the amount of addition $\alpha$ is other than 1.

The gain circuit 44 performs gain adjustment of:

$$B = (1+\alpha) \cdot B1 \quad (2)$$

on the image pickup signal B1 for each pixel.

Furthermore, the output signal of the addition circuit 43 and the output signal of the gain circuit 44 are switched by a switching circuit 45 according to the determination result of the determination circuit 42, and one of the output signals is selected and outputted as the image signal B.

As described above, the image pickup signal G is always multiplied by the coefficient $\beta(=(\alpha+1)/k)$. Thus, an adjustment is made for reducing different radiation light quantities as shown in FIG. 3B between the narrow band illumination light beam G and two narrow band illumination light beams B1 and B2 so as to achieve the balance in brightness between the image signal G and the image signal B subjected to an aligned addition or gain adjustment.

The determination circuit 42 detects an amount of shift (or amount of misalignment) necessary for alignment for performing an aligned addition on the addition circuit 43 and outputs this amount of shift to the addition circuit 43. The determination circuit 42 controls the addition circuit 43 so as to perform an addition by shifting image signals by an amount of shift, that is, perform an aligned addition and also controls the switching of the switching circuit 45.

An amount of addition $\alpha$ is inputted to the addition circuit 43 as a coefficient when an addition from the control section 17 is performed. This amount of addition $\alpha$ is set within a range of $0 \leq \alpha \leq 1$ by the control section 17.

Furthermore, the determination circuit 42 determines a normalized cross-correlation between the two image pickup signals B1 and B2.

The normalized cross-correlation is determined by calculating a cross-correlation when, with respect to one image pickup signal B1, the other corresponding image pickup signal B2 is shifted in one-pixel units within a range of up to several pixels (e.g., 5 pixels) in the horizontal and vertical directions and dividing the cross-correlation by the square root of the sum of squares of signal intensities at the respective pixels of the image pickup signal B1. The determination circuit 42 determines whether or not a maximum value in a plurality of normalized cross-correlations exceeds a threshold. The range from which the normalized cross-correlations are determined in this case are not limited to the case with several pixels.

In order to obtain the normalized cross-correlations, the determination circuit 42 sets a plurality of (four in FIG. 6) local regions shown by a diagonally shaded area in the picked-up image (corresponding to one frame) of the image pickup signal B1 as shown, for example, in FIG. 6 and likewise sets local regions corresponding thereto for the picked-up image of the image pickup signal B2 as shown on the right thereof. When, for example, the local regions on the right side are shifted in one-pixel units in horizontal and vertical directions within a range of up to several pixels, the respective normalized cross-correlations are determined for every plurality of local regions.

Thus, the determination circuit 42 determines the case where the maximum value of the calculated normalized cross-correlations exceeds a threshold which is a criterion relative to which the correlation can be regarded to be large and the case where the maximum value is equal to or below the threshold, and controls the switching of the switching circuit 45 according to the determination result.

That is, the determination circuit 42 selects the output signal of the gain circuit 44 when the normalized cross-correlation $\leq$ threshold or selects the output signal of the addition circuit 43 when the normalized cross-correlation > threshold.

When the maximum value of the calculated normalized cross-correlations exceeds the threshold, the determination circuit 42 outputs an amount of shift that gives the maximum value to the addition circuit 43.

The addition circuit 43 then shifts the image pickup signal B2 by the amount of shift, performs processing of an aligned addition on the image pickup signals B1 and B2 as expressed by Equation 1 and outputs the synthetic image resulting from the processing to the switching circuit 45.

Instead of causing the addition circuit 43 to generate a synthetic image according to the determination result indicating that the normalized cross-correlation≦threshold, the determination circuit 42 may perform control so that the gain circuit 44 generates an alternate image.

FIG. 7 illustrates processing contents of the determination circuit 42, the addition circuit 43, the gain circuit 44 and the switching circuit 45 in the image processing circuit 35. When the operation of the image processing circuit 35 starts, the determination circuit 42 determines a normalized cross-correlation between both picked-up images of the image pickup signals B1 and B2 as shown in step S1. In FIG. 7, the normalized cross-correlation is illustrated, simplified as "correlation". That is, as shown in FIG. 6, the determination circuit 42 calculates a normalized cross-correlation between the local regions of the image pickup signals B1 and B2.

In next step S2, the determination circuit 42 determines whether or not even any one of the normalized cross-correlations determined for every plurality of local regions exceeds a threshold. Instead of determining whether or not any one of the normalized cross-correlations determined for every plurality of local regions exceeds a threshold, the determination circuit 42 in this case may determine whether or not normalized cross-correlations in two or more local regions exceed a threshold. Alternatively, the determination circuit 42 may determine whether or not normalized cross-correlations of a majority of local regions exceed a threshold. When the determination result shows that the normalized cross-correlations exceed the threshold, the addition circuit 43 performs addition processing in steps S3 and S4.

That is, the addition circuit 43 performs pixel shifting processing as shown in step S3. Through the pixel shifting processing, the addition circuit 43 sets the picked-up image of the image pickup signal B2 in a state in which the correlation value with respect to the picked-up image of the image pickup signal B1 becomes a maximum.

In next step S4, the addition circuit 43 performs addition processing whereby both picked-up images of both image pickup signals B1 and B2 are aligned with each other and added up to generate a synthetic image.

Through step S3 and step S4, an aligned image resulting from superimposing and adding up both picked-up images of the image pickup signals B1 and B2 is generated as a synthetic image. The image pickup signal of the aligned image after addition processing is subjected to switching processing by the switching circuit 45 (step S5) and outputted from the image processing circuit 35 as an image signal B.

On the other hand, when the determination result in step S2 shows that the normalized cross-correlation is equal to or below the threshold, in step S6, the gain circuit 44 as an alternate image generation section gain-adjusts the image pickup signal B1 by multiplying $(1+\alpha)$-fold and outputs the gain-adjusted image pickup signal B1 as an alternate image. The gain-adjusted image pickup signal B1 is outputted from the image processing circuit 35 via the switching circuit 45 as an image signal B.

Instead of performing an addition or gain adjustment in Equation 1 or Equation 2, image signals G' and B' to be outputted from the image processing circuit 35 may be calculated (as image signals G and B) through the matrix calculation in Equation 3 on the image pickup signals G, B1 and B2 inputted according to the determination result of the determination circuit 42.

In the case of an addition, Mat1 may be selected as Mat in Equation 3, and in the case of gain adjustment, Mat2 may be selected as Mat.

[Equation 3]

$$\begin{bmatrix} G' \\ B' \end{bmatrix} = Mat \begin{bmatrix} B2 \\ G \\ B1 \end{bmatrix} \quad Mat1 = \begin{bmatrix} 0 & \beta & 0 \\ \alpha & 0 & 1 \end{bmatrix} \quad Mat2 = \begin{bmatrix} 0 & \beta & 0 \\ 0 & 0 & (1+\alpha) \end{bmatrix} \quad (3)$$

The image signal subjected to the predetermined signal processing by the image processing circuit 35 is color-converted by a color conversion circuit 67. The color conversion circuit 67 performs color conversion from the inputted image signals G and B as expressed in Equation 5, which will be described later, and outputs the image signals R, G and B to the D/A conversion circuit 36. The image signals R, G and B are converted from digital signals to analog signals by the D/A conversion circuit 36, and then outputted to the monitor 5. The color conversion circuit 67 sets parameters when performing color conversion via the control section 17. The image signals G and B may be outputted to the monitor 5 via the D/A conversion circuit 36 without passing through the color conversion circuit 36.

In the case of FIG. 1, the color-converted image signals R, G and B are inputted to the R, G and B channels of the monitor 5 and displayed in three colors on the monitor 5.

The type detection circuit 18 detects type information of the connected endoscope 2A based on the ID information of the endoscope 2A outputted from the scope ID generation section 14 and outputs the type information to the control section 17.

When the detected type is a specific endoscope type, the control section 17 does not perform addition processing by the above described addition circuit 43.

The operation when using the endoscope apparatus 1A in such a configuration will be described.

When using the endoscope apparatus 1A, the operator connects the light source connector 20 of the endoscope 2A to the light source section 3A as shown in FIG. 1 and connects a signal connector (not shown) of the endoscope 2A to the processor 4A.

After the connections are set as shown in FIG. 1, the operator operates a power switch (not shown) to make the light source section 3A, the processor 4A and the monitor 5 start operating. The control section 17 then performs control to make narrow band observations on the light source section 3A and the processor 4A.

When the operator operates the scope switch 13 or the like and the observations start, the control section 17 drives the motor 27 to rotate.

Since the G filter 6G and B filters 6B1 and 6B2 of the revolving filter 25 are sequentially inserted in the optical path of the xenon lamp 22, illumination light beams of narrow band G, B1 and B2 of the light radiated from the xenon lamp 22 are sequentially allowed to pass and the respective illumination light beams are radiated onto the subject side via the light guide fiber 19 at periods of $\frac{1}{20}$ seconds sequentially and substantially consecutively.

At the respective timings at which the illumination light beams of G, B1 and B2 are radiated onto the same region of the subject, the CCD 11 picks up optical images of the region. That is, the CCD 11 converts the respective picked-up images of reflected light images from the region (in a broader sense, returning light images) to their respective image pickup signals G, B1 and B2 and outputs the signals to the processor 4A.

The image pickup signals B1 and B2 are image pickup signals picked up with the same wavelength and the same exposure quantity, that is, under substantially the same condition (except the existence of a short timing shift within one frame).

The image pickup signals G, B1 and B2 inputted to the processor 4A are amplified and subjected to A/D conversion at the respective sections of the processor 4A and recorded in the first frame memory 34a, the second frame memory 34b and the third frame memory 34c respectively with their recording destinations sequentially switched under the switching control of the multiplexer 33 by the control section 17.

As shown in FIG. 1, the image pickup signals G, B1 and B2 recorded in the first frame memory 34a, the second frame memory 34b and the third frame memory 34c are read in synchronization with each other, for example, at periods of 1/20 seconds and outputted to the image processing circuit 35.

The image processing circuit 35 performs the processing operation as shown in FIG. 7. The image signals G and B generated by the image processing circuit 35 are color-converted to image signals R, G and B by the color conversion circuit 67, then converted from digital to analog and displayed on the monitor 5.

Furthermore, in the present embodiment, the control section 17 performs a control operation as shown in FIG. 8 so that brightness of the picked-up images is set to a target brightness value that makes the images easy to observe.

The control section 17 controls the light quantity control circuit 24, the AGC circuit 31 and the addition circuit 43 shown in FIG. 4 according to the relationship between brightness detection of the picked-up images and brightness target values as shown in FIG. 8. The control section 17 may also perform control including the gain circuit 44 shown in FIG. 5 or FIG. 12 in addition to the addition circuit 43 or the like. Furthermore, the control section 17 may also perform control including a weighted averaging circuit 74 in FIG. 23 in a fourth embodiment which will be described later. In the case of the fourth embodiment, the control section 17 may also adjust brightness by adjusting the value of a in Equation 8 which will be described later.

When the endoscope apparatus 1A is set in an operating state, the control section 17 determines whether or not the picked-up image is bright, as shown in step S11, using a light adjustment signal from the light adjustment circuit 37.

Upon determining that the picked-up image picked up using the CCD 11 is brighter than the target value based on the light adjustment signal from the light adjustment circuit 37, the control section 17 moves to control processing in step S12. In step S2, the control section 17 determines whether or not the AGC gain when controlling the AGC operation of the AGC circuit 31 is a minimum value.

When the AGC gain is not a minimum value, as shown in step S13, the control section 17 decreases the control signal level of the AGC gain so as to reduce the AGC gain by a predetermined amount and then returns to the processing in step S11.

On the other hand, when the control section 17 determines that the picked-up image is brighter even when the AGC gain is a minimum value, the control section 17 moves to step S14.

In step S14, the control section 17 determines whether or not the amount of addition $\alpha$ is a minimum value when the addition circuit 43 performs an addition.

When the amount of addition $\alpha$ is not a minimum value, in step S15, the control section 17 reduces the value of the amount of addition $\alpha$ by a predetermined amount and then returns to the processing in step S11.

On the other hand, when the picked-up image is bright even when the amount of addition $\alpha$ is a minimum value and the AGC gain is also a minimum value, in step S16, the control section 17 determines whether or not the diaphragm 23 is fully closed.

When the diaphragm 23 is not fully closed, in step S17, the control section 17 controls the diaphragm 23 so as to close by a predetermined amount and returns to the processing in step S11. Furthermore, when the diaphragm 23 is also fully closed, the control section 17 returns to the processing in step S11.

On the other hand, when the determination processing result in step S11 shows that the picked-up image is not bright, that is, the picked-up image is determined to have brightness less than a target value, the control section 17 moves to the processing in step S18. In step S18, the control section 17 determines whether or not the diaphragm 23 is fully open.

When the diaphragm 23 is not fully open, in step S19, the control section 17 performs control so as to fully open the diaphragm 23 and then returns to the processing in step S11.

On the other hand, when the diaphragm 23 is fully open, in step S20, the control section 17 determines whether or not the amount of addition $\alpha$ is a maximum value. When the amount of addition $\alpha$ is not a maximum value, in step S21, the control section 17 performs control of increasing the amount of addition $\alpha$ by a predetermined amount and then returns to the processing in step S11.

When the amount of addition $\alpha$ in step S20 is a maximum value, that is, the target brightness value is not reached even if the diaphragm 23 is fully opened and the amount of addition $\alpha$ is set to a maximum value, in step S22, the control section 17 determines whether or not the AGC gain is a maximum value.

When the AGC gain is not a maximum value, in step S23, the control section 17 performs control so as to increase the AGC gain by a predetermined amount and then returns to the processing in step S11. Furthermore, even when the AGC gain is a maximum value, the control section 17 returns to the processing in step S11.

When the brightness of the picked-up image is dark because of the control operation shown in FIG. 8, that is, when the target value is not reached, the control section 17 performs control on brightness adjustment in order, giving the highest priority to a light quantity by the diaphragm 23, the next highest priority to the amount of addition $\alpha$ by the addition circuit 43 and the lowest priority to the AGC gain by the AGC circuit 31.

On the other hand, when the brightness of the picked-up image is equal to or above the target value, the control section 17 performs control so as to adjust brightness in the order reverse to that of the above described case where the brightness is dark. That is, the control section 17 performs control so as to adjust picked-up images with low priority first and leave those with high priority.

Through the above described brightness adjustment control, brightness adjustment as shown in FIG. 9 is performed according to the observation distance from the distal end of the insertion portion 7 of the endoscope 2A to the region of the observation target (image pickup target).

On the short distance side where the observation distance is small as shown in FIG. 9, the amount of opening of the diaphragm 23 increases as the observation distance increases. Furthermore, as the observation distance increases, the amount of opening is fully open (open) at a certain observation distance D1. When the observation distance is greater than the observation distance D1, the amount of addition α of the addition circuit 43 increases from 0 while the diaphragm 23 remains fully open.

When the observation distance is greater than the observation distance D2 at which the amount of addition α has reached the maximum value, the AGC gain of the AGC circuit 31 increases from the minimum value.

According to the present embodiment that performs such brightness adjustment, the same narrow band illumination light is radiated onto the same region to be observed twice within a one-frame period, images are added up and a synthetic image is generated in consideration of the amount of pixel misalignment between images picked up at the same exposure quantity, and therefore images with a high S/N can be generated.

By contrast, for example, in the related art of Japanese Patent Application Laid-Open Publication No. 11-234662, an image is synthesized with one image picked up with a reduced exposure quantity compared to the other, and therefore the S/N decreases. Furthermore, the present embodiment does not simply add up two images, but detects the amount of misalignment between the images and performs an aligned addition using the amount of misalignment to generate a synthetic image, and can thereby prevent deterioration of image quality that occurs when two images are simply added up, according to the amount of misalignment and generate an image with a high S/N.

In the aforementioned description, when the diaphragm 23 of the light source section 3A performs light quantity adjustment to adjust brightness, the control section 17 may control the CCD drive circuit 15 so as to perform electronic shuttering when acquiring an image pickup signal G under narrow band illumination light through the G filter 6G. This is intended to reduce influences of the fact that the outgoing light quantity of G is greater than the outgoing light quantity of the other B as shown in FIG. 3B.

That is, it may be possible to shorten an exposure time (compared to cases of other B1 and B2) when acquiring the image pickup signal G in synchronization with the period during which illumination of G of a narrow band is performed and the image pickup signal G may be acquired in the shortened exposure time.

By so doing, when images are balanced in color (corresponding to white balance under wideband illumination light) under narrow band illumination light, it is possible to reduce the possibility that the image pickup signal G may be more likely to saturate due to color balancing (the dynamic range is narrowed due to color balancing with an unbalanced outgoing light quantity) and the possibility that that images may be unnaturally colored due to charge saturation of the CCD.

Next, a modification example of the present embodiment will be described. The first embodiment has described that narrow band illumination light is radiated onto the same region twice within a one-frame period, the respective picked-up images are synthesized through an aligned addition in consideration of the amount of pixel misalignment between both images to generate an aligned image as a synthetic image, and it is thereby possible to generate an image with a high S/N.

Even when narrow band illumination light is radiated onto the same region three times or more within a one-frame period, the present embodiment can generate an image with a high S/N. A modification example which will be described below corresponds to such a case.

Figure 10:
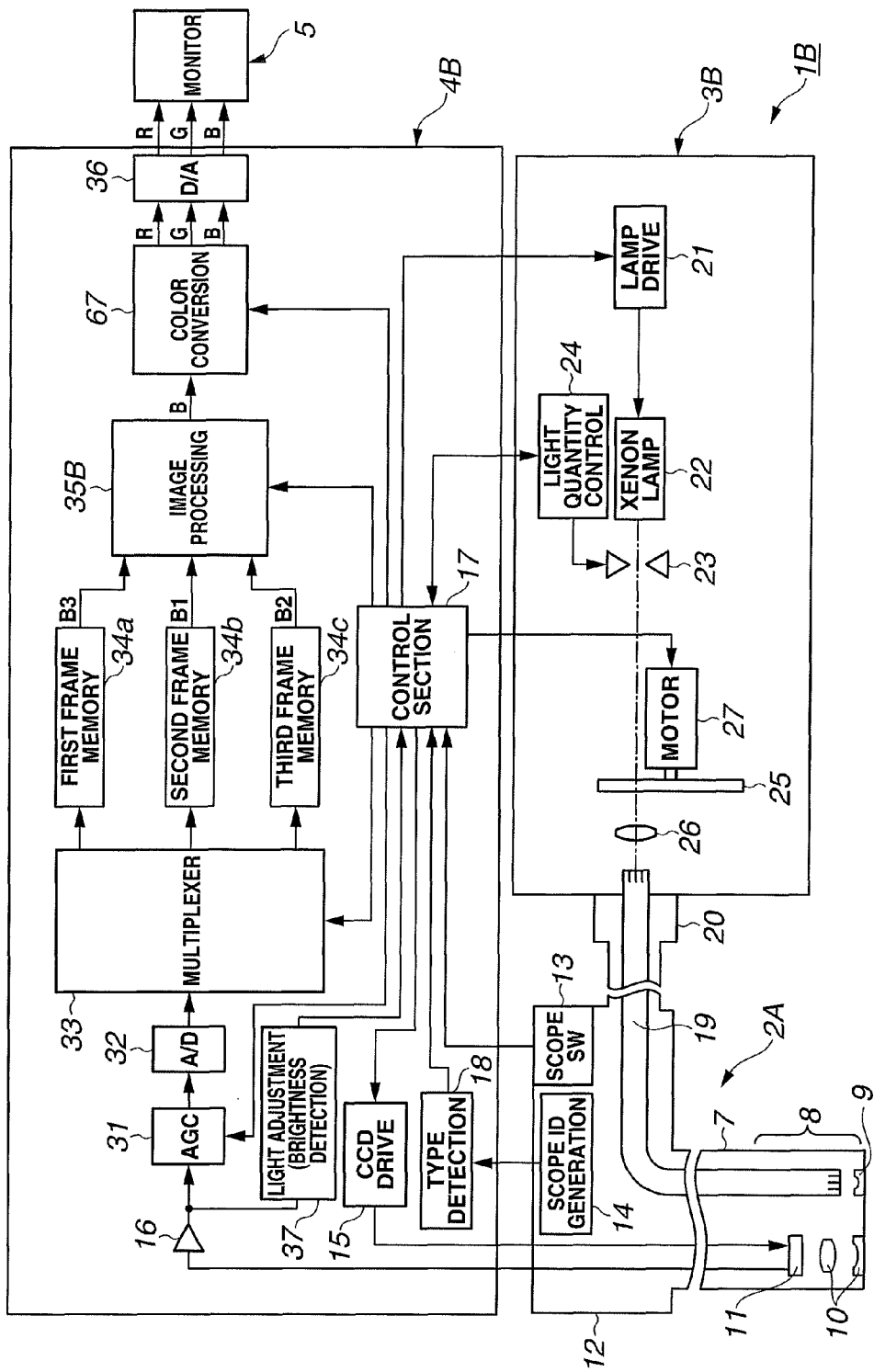
FIG. 10 is a diagram illustrating an overall configuration of an endoscope apparatus according to a modification example of the first embodiment.

FIG. 10 illustrates an endoscope apparatus 1B of a modification example. The endoscope apparatus 1B adopts a light source section 3B that uses a narrow band B3 filter 6B3 instead of the G filter 6G attached to the revolving filter 25 in the light source section 3A of the endoscope apparatus 1A in FIG. 1.

Figure 11:
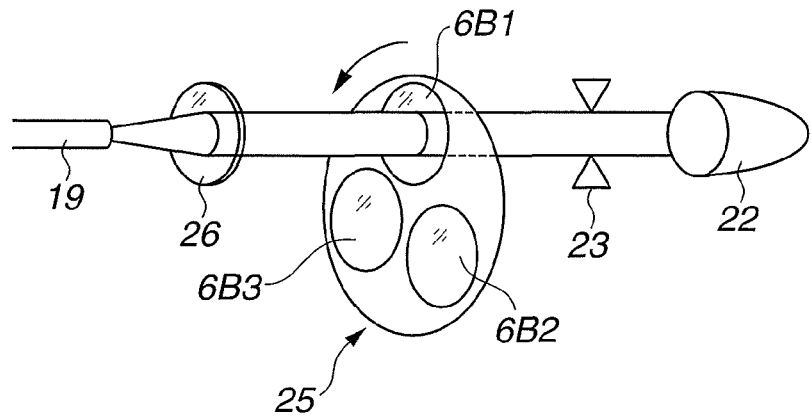
FIG. 11 is a diagram illustrating a configuration of the revolving filter peripheral section in the light source section according to the modification example of the first embodiment.

FIG. 11 illustrates a peripheral section of the revolving filter 25 of the light source section 3B in the present modification example. The revolving filter 25 is provided with narrow band B filters 6B1, 6B2 and 6B3 of the same transmission characteristics in a circumferential direction.

Furthermore, accompanying the adoption of the light source section 3B, the present modification example adopts a processor 4B using an image processing circuit 35B obtained by partially modifying the image processing circuit 35 in the processor 4A in FIG. 1. In such a configuration, as shown in FIG. 10, the first frame memory 34a stores an image pickup signal B3 picked up under illumination light of the B filter 6B3 instead of the image pickup signal G. Furthermore, three image pickup signals B3, B1 and B2 are inputted to the image processing circuit 35B as shown in FIG. 12.

Figure 12:
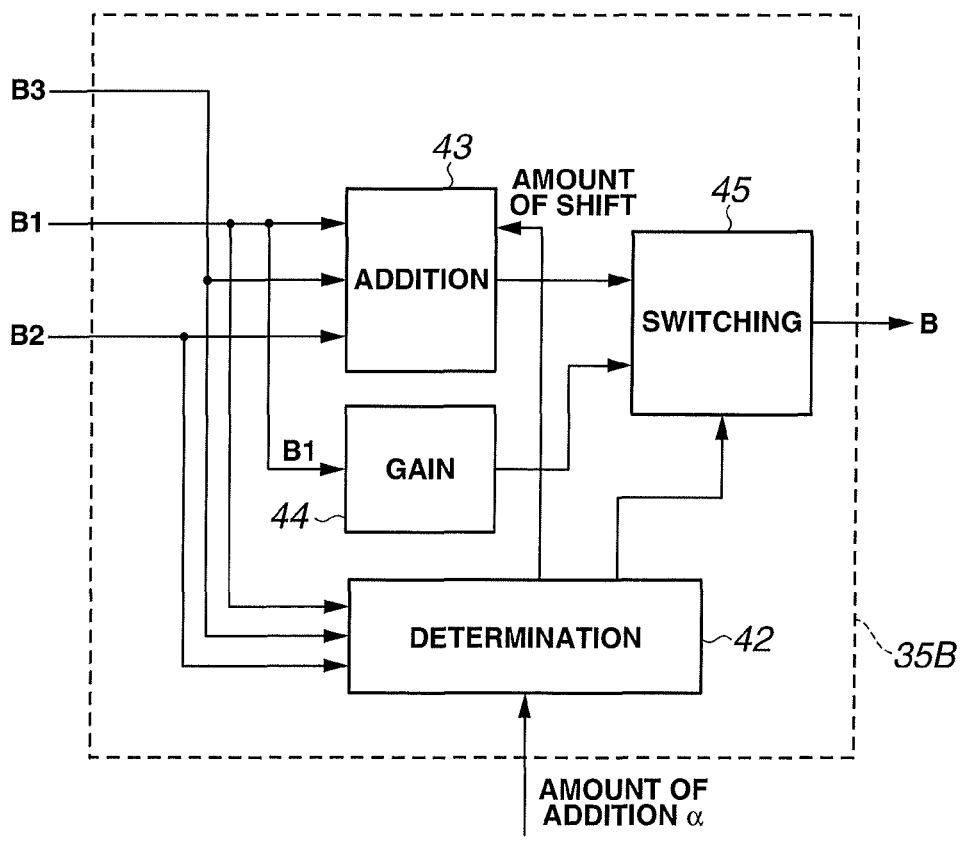
FIG. 12 is a block diagram illustrating a configuration of the image processing circuit according to the modification example of the first embodiment.

The image processing circuit 35B shown in FIG. 12 adopts the configuration of the image processing circuit 35 shown in FIG. 5 without the multiplication circuit 41 and also adopts a configuration in which three image pickup signals B3, B1 and B2 are inputted to the determination circuit 42 and the addition circuit 43.

In the image processing circuit 35B, the determination circuit 42 calculates a normalized cross-correlation between the image pickup signals B1 and B2 in the same way as the first embodiment and calculates an amount of shift (amount of misalignment) of the image pickup signal B2 using the image pickup signal B1 as a reference. Furthermore, the determination circuit 42 in this case performs processing between the image pickup signals B1 and B3 similar to that in the case of the image pickup signals B1 and B2. The determination circuit 42 then calculates an amount of shift of the image pickup signal B3 using the image pickup signal B1 as a reference.

Furthermore, the addition circuit 43 shifts pixels of the images of the image pickup signals B2 and B3 based on the amount of shift according to the determination circuit 42 and then adds the images to the image of the image pickup signal B1. That is, image processing of generating an aligned image is also performed in the case of the present modification example.

The image processing circuit 35B then outputs the image pickup signal B1 gain-adjusted by the addition circuit 43 or gain circuit 44 via the switching circuit 45 as an image signal B. In the case of an addition, an image signal if to be outputted from the image processing circuit 35 is obtained (as the image signal B) through a matrix calculation in Equation 4.

[Equation 4]

$$\begin{bmatrix} 0 \\ 0 \\ B' \end{bmatrix} = Mat3 \begin{bmatrix} B_2 \\ B_3 \\ B_1 \end{bmatrix} \quad Mat3 = \begin{bmatrix} 0 & 0 & 0 \\ 0 & 0 & 0 \\ \alpha & \alpha & 1 \end{bmatrix} \quad (4)$$

$$0 \leq \alpha \leq 1$$

Here, the coefficient α used for the conversion as described above is a value from 0 to 1. In this case, the image signal B is inputted, for example, to the channel of B of the monitor 5. The image signal B may also be inputted to the respective channels of R, G and B and displayed in black and white.

The present modification example radiates narrow band illumination light three times within a one-frame period, calculates an amount of misalignment between picked-up images obtained respectively and adds up the picked-up images so as to superimpose on each other, and can thereby generate an image with a high S/N as in the case of the first embodiment.

When the vicinity of the mucous membrane surface of a living body is observed (image is picked up) as a region to be observed, using the narrow band wavelength light of B makes it possible to generate an image of the state in the vicinity of the surface layer that can be easily observed in details by reducing influences of light reflected from the depth rather than from the surface layer.

The present modification example adopts narrow band light of B3 instead of narrow band light of G in the first embodiment, but it may also be possible to adopt a configuration in which the number of openings of the revolving filter 25 in the first embodiment is incremented by 1 from 3 to 4 and the B filter B3 is provided in the added opening. Narrow band image signals G and B may be generated.

Second Embodiment

Figure 13:
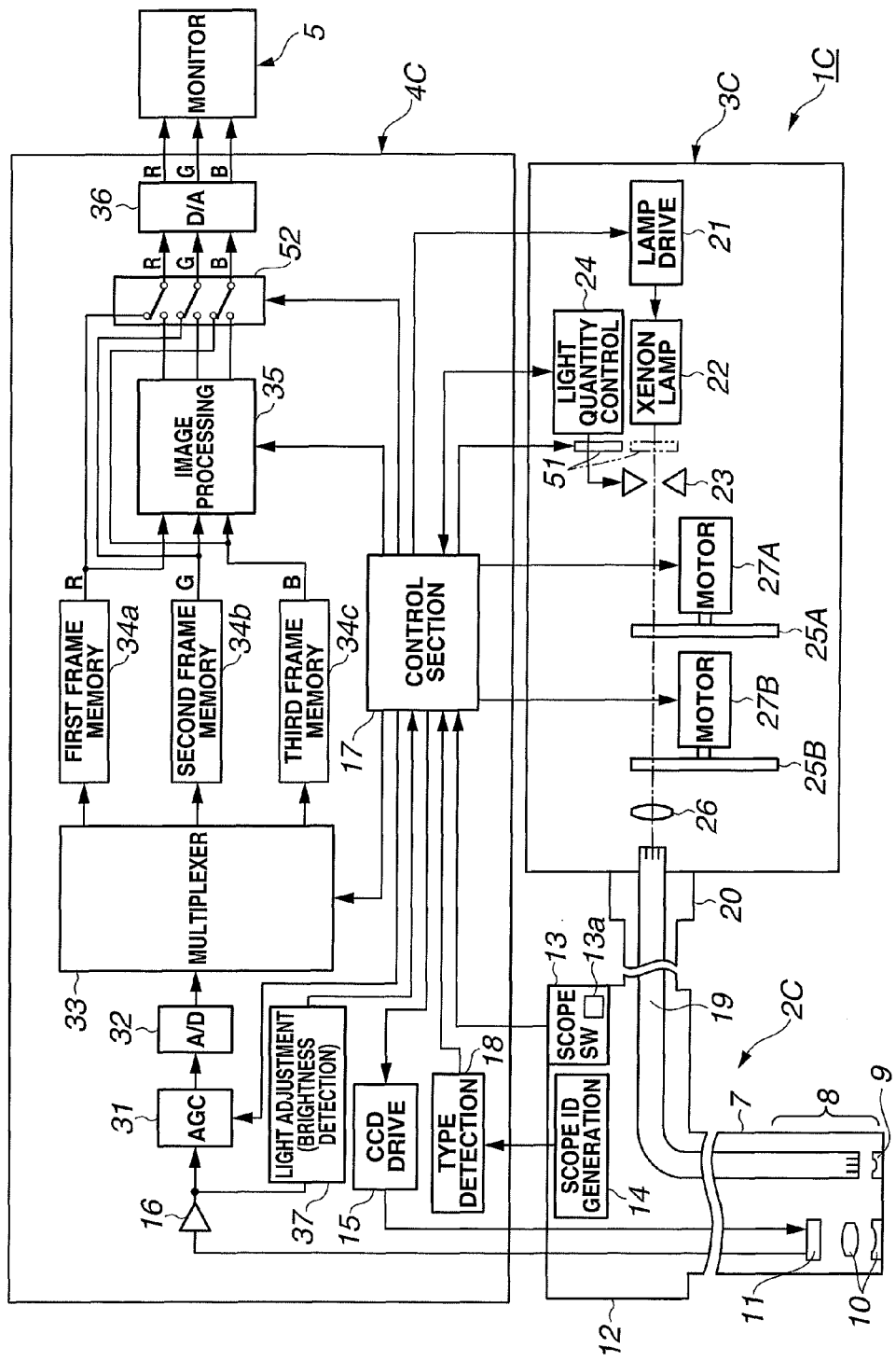
FIG. 13 is a diagram illustrating an overall configuration of an endoscope apparatus according to a second embodiment of the present invention.

Next, a second embodiment of the present invention will be described with reference to FIG. 13. FIG. 13 illustrates a configuration of an endoscope apparatus 1C according to the second embodiment of the present invention. The endoscope apparatus 1A of the first embodiment is a narrow band observation endoscope apparatus that makes an endoscope observation using narrow band illumination light.

By contrast, the endoscope apparatus 1C of the present embodiment is an endoscope apparatus that can select and use a normal observation mode in which a normal observation, that is, an endoscope observation under wideband illumination light is made or the narrow band observation mode (hereinafter, referred to as an "NBI observation mode") described in the first embodiment.

Thus, the endoscope apparatus 1C of the present embodiment is constructed of an endoscope 2C, a light source section 3C that generates illumination light of R, G and B as wideband visible region illumination light and narrow band illumination light of G, B1 and B2 (also referred to as NBI-G, NBI-B1 and NBI-B2) as in the case of the first embodiment, a processor 4C and the monitor 5.

The endoscope 2C corresponds to the endoscope 2A in FIG. 1 with the scope switch 13 provided with an observation mode changeover switch 13a that switches between observation modes. When the operator operates the observation mode changeover switch 13a, the control section 17 performs control of switching illumination light emitted from the light source section 3C and switches the operation of the image processing circuit 35 in the processor 4C.

The light source section 3C in the present embodiment corresponds to the light source section 3A in FIG. 1 provided with an option filter 51 disposed between the xenon lamp 22 and the diaphragm 23 in a manner detachable from the optical path, and two revolving filters 25A and 25B disposed between the diaphragm 23 and the condenser lens 26. The revolving filters 25A and 25B are driven to rotate by motors 27A and 27B respectively and both motors 27A and 27B rotate in synchronization with each other under the control of the control section 17.

Figure 14A:
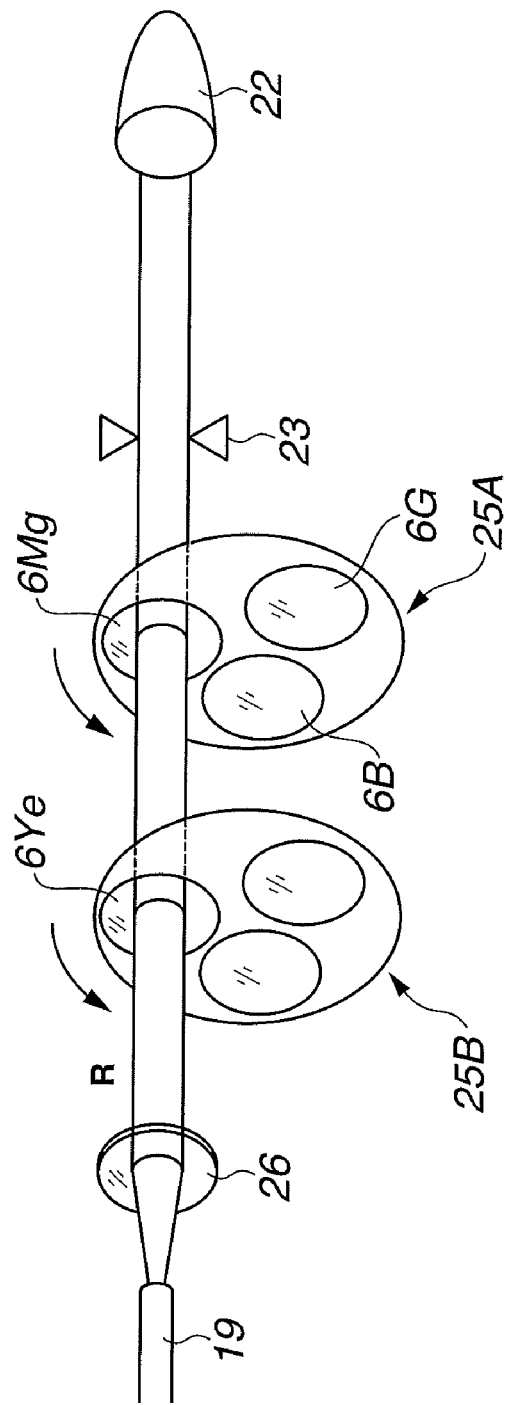
FIG. 14A is a diagram illustrating a setting state of the revolving filter peripheral section of the light source section in a normal observation mode and an NBI observation mode.
Figure 14B:
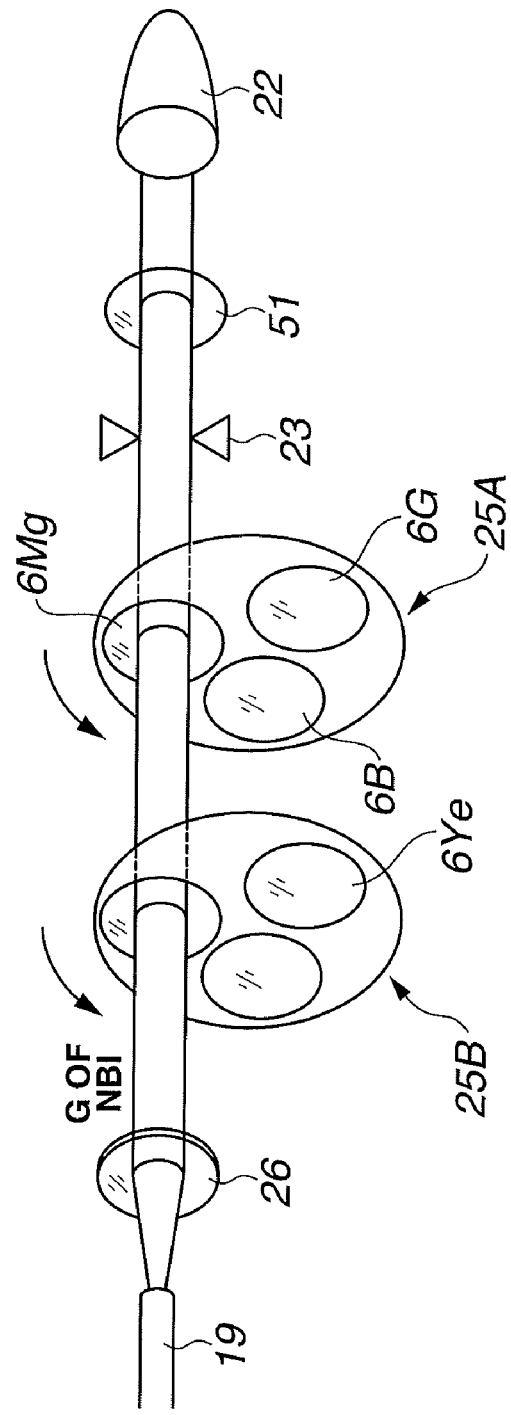
FIG. 14B is a diagram illustrating a setting state of the revolving filter peripheral section of the light source section in the normal observation mode and the NBI observation mode.

FIG. 14A and FIG. 14B illustrate a configuration of the revolving filter peripheral section of the present embodiment, FIG. 14A illustrates a state of the normal observation mode and FIG. 14B illustrates a state of the NBI observation mode.

The option filter 51 is removed from the optical path in the normal observation mode as shown in FIG. 14A, whereas the option filter 51 is disposed on the optical path in the NBI observation mode as shown in FIG. 14B.

Furthermore, the option filter 51 is inserted or removed into/from the optical path by the control section 17 via a filter inserting/removing apparatus (not shown). The option filter 51 has NBI-G and NBI-B transmission characteristics. To be more specific, the option filter 51 has narrow band transmission characteristics which also include the transmission characteristics of the filters 6G and 6B1 (or 6B2) shown in FIG. 3A.

Furthermore, the two revolving filters 25A and 25B are provided with three openings in their circumferential directions at equal angles respectively and provided with filters 6Mg, 6G and 6B that allow to pass wide wavelength bands of Mg (magenta), G and B respectively and one filter 6Ye that allows to pass a wide Ye (yellow color) wavelength band.

The revolving filter 25B is provided with only one Ye filter 6Ye and the remaining two openings have no filter (or a transparent filter having transparent transmission characteristics). The two revolving filters 25A and 25B rotate in synchronization with each other.

Furthermore, of the two revolving filters 25A and 25B, for example, the rotation phase of the revolving filter 25B is shifted by 120° between the normal observation mode and the NBI observation mode.

To be more specific, in a state of the normal observation mode, when the filters 6Mg, 6G and 6B of the revolving filter 25A are sequentially arranged on the optical path, the filter 6Ye, no filter and no filter of the revolving filter 25B are sequentially arranged on the optical path. In this case, frame sequential illumination light beams of widebands R, G and B are generated and supplied to the light guide fiber 19.

On the other hand, in the NBI observation mode, the option filter 51 is disposed on the optical path all the time as shown in FIG. 14B. When the filters 6Mg, 6G and 6B of the revolving filter 25A are sequentially arranged on the optical path, no filter, filter 6Ye and no filter of the revolving filter 25B are sequentially arranged on the optical path in synchronization with this. Therefore, in the NBI observation mode, illumination light passes through the option filter 51 and the filter 6Mg, the option filter 51 and the filters 6G and 6Ye, the option filter 51 and the filter 6B respectively. That is, illumination light beams of narrow band B2, G and B1 are sequentially generated.

Furthermore, the processor 4C includes a changeover switch 52, which is switched by the control section 17, provided at the output end of the image processing circuit 35 of the processor 4A in FIG. 1. In the normal observation mode, the control section 17 switches the changeover switch 52 so as to bypass the image processing circuit 35 and output to the subsequent stage.

Instead of bypassing the image processing circuit 35, when a circuit for enhancing contours or the like is added in the image processing circuit 35 and the mode is switched to the normal observation mode, contours enhancement or the like may also be performed.

By contrast, in the NBI observation mode, image pickup signals G, B1 and B2 temporarily stored in the first frame memory 34a, the second frame memory 34b and the third frame memory 34c are inputted to the image processing circuit 35 as in the case of the first embodiment.

The rest of the configuration is the same as that of the first embodiment.

Figure 15:
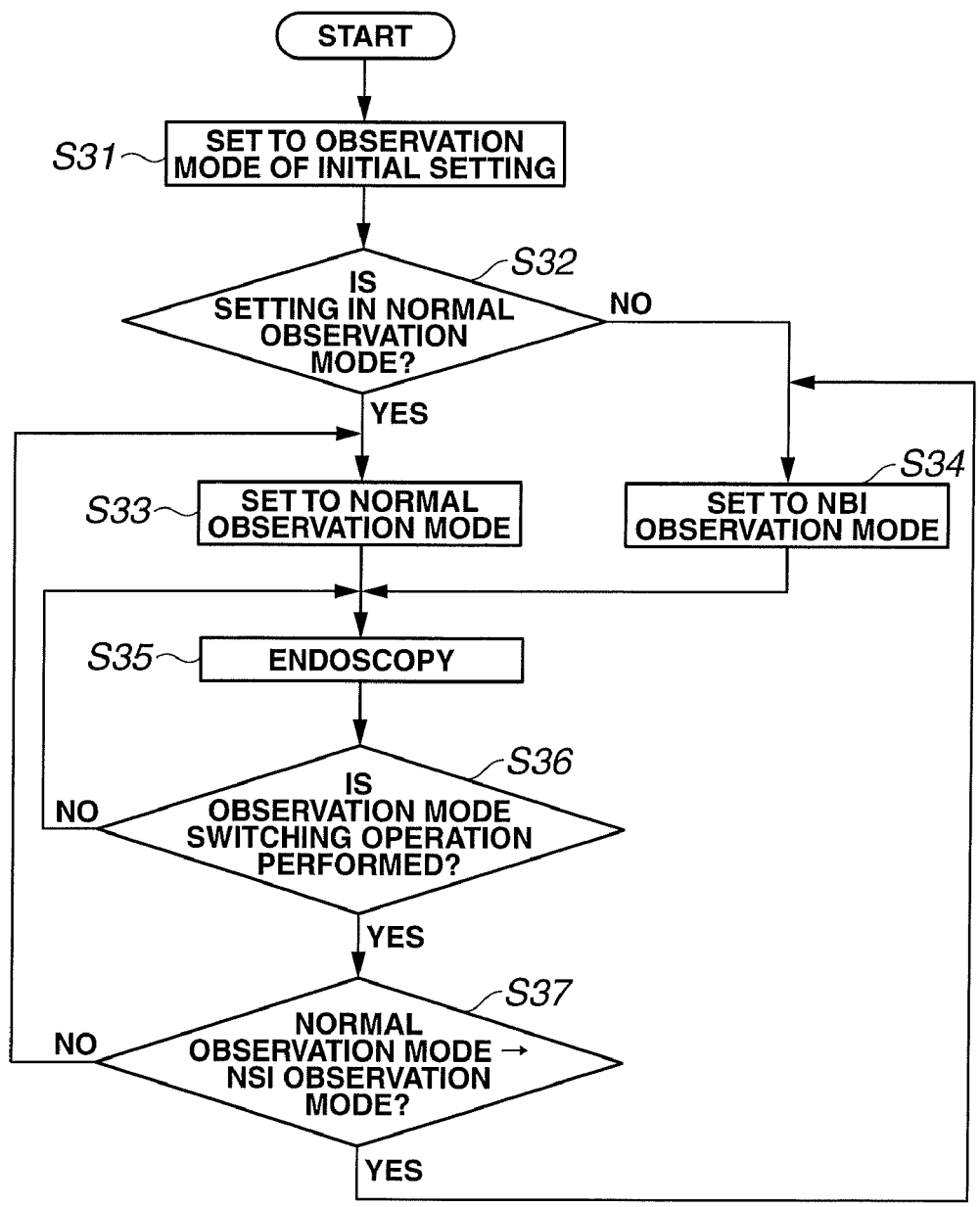
FIG. 15 is a flowchart illustrating operation contents according to the second embodiment.

Next, the operation of the present embodiment will be described with reference to FIG. 15.

While the first embodiment has only the NBI observation mode, the present embodiment is designed to be able to select and use the normal observation mode or the NBI observation mode.

When the endoscope apparatus 1C is placed in an operating state by turning on the power, the control section 17 performs control so that a setting state corresponding to the initial setting is set as shown in step S31.

As shown in step S32, the control section 17 determines whether or not the initial setting is a setting in the normal observation mode. When the initial setting is the setting in the normal observation mode, the control section 17 performs control so as to set the light source section 3C and the processor 4C in a setting state in the normal observation mode as shown in step S33.

By contrast, when the initial setting is set to the NBI observation mode, the control section 17 performs control so as to set the light source section 3C and the processor 4C in a setting state in the NBI observation mode as shown in step S34.

When the initial setting is set to the normal observation mode, the endoscope apparatus 1C operates in a setting state in the normal observation mode as shown in FIG. 13.

The operator can then perform endoscopy in the normal observation mode as shown in step S35.

In the setting state in the normal observation mode, the light source section 3C supplies wideband R, G and B frame sequential illumination light beams to the light guide fiber 19 of the endoscope 2C and the wideband R, G and B frame sequential illumination light beams from the illumination window of the distal end portion 8 are radiated onto a region of the subject. The reflected light reflected by the region of the subject, namely, the returning light from the region of the subject forms an image on the image pickup surface of the CCD 11 through the objective lens 10.

The CCD 11 sequentially outputs the image pickup signals of R, G and B picked up under the wideband R, G and B frame sequential illumination light beams to the processor 4C. The image pickup signals R, G and B are amplified by the preamplifier 16, subjected to AGC control by the AGC circuit 31 so as to have predetermined amplitude and then converted to digital image pickup signals R, G and B by the A/D conversion circuit 32.

The digital image pickup signals R, G and B are sequentially stored in the first frame memory 34a, the second frame memory 34b and the third frame memory 34c via the multiplexer 33 and simultaneously read. The digital image pickup signals R, G and B are then inputted to the R, G and B channels of the monitor 5 as analog image signals synchronized by the D/A conversion circuit 36 and displayed in color on the monitor 5 as an endoscope image.

When desiring to observe details of the vicinity of the surface layer of the mucous membrane in the middle of endoscopy, the operator operates the observation mode changeover switch 13a. The control section 17 is monitoring the operation of the observation mode changeover switch 13a, for example, at fixed periods as shown in step S36.

When the observation mode changeover switch 13a is not operated, endoscopy can be continued in the same observation mode.

On the other hand, when the observation mode changeover switch 13a is operated, the control section 17 determines whether or not to instruct switching from the normal observation mode to the NBI observation mode as shown in step S37. When this case corresponds to the switching instruction, the control section 17 moves to the processing in step S34.

In step S34, the control section 17 sets the light source section 3C in a state in which the narrow band G, B1 and B2 illumination light beams shown in FIG. 14B are emitted. Furthermore, the processor 4C is set in a setting state similar to that shown in FIG. 1. The endoscopy as shown in step S35 can be then performed. The operation in this case is an operation similar to that of the first embodiment. Furthermore, similar effects are obtained.

In this state, the control section 17 is also monitoring the operation of the observation mode changeover switch 13a, for example, at fixed periods as shown in step S36. When the switching is operated, the control section 17 determines the switching instruction in step S37 and controls the setting of switching to the normal observation mode in step S33.

According to the present embodiment that operates in this way, it is possible to perform endoscopy in a normal visible region in the normal observation mode and also generate an image with a high S/N of narrow band observation under narrow band illumination light as in the case of the first embodiment. It is possible to supply an image easy to diagnose with a high S/N to the operator.

Third Embodiment

Figure 16:
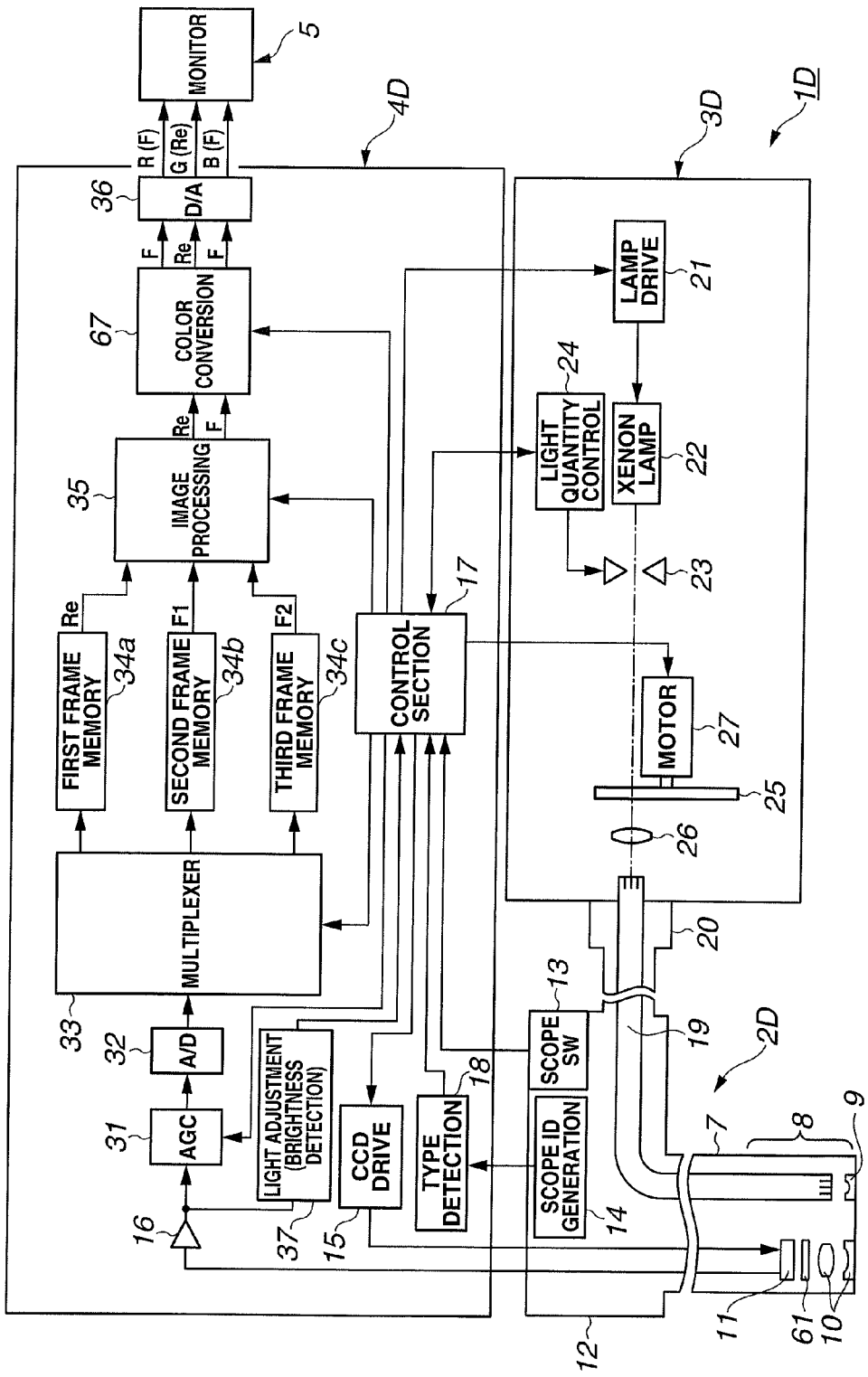
FIG. 16 is a diagram illustrating an overall configuration of an endoscope apparatus according to a third embodiment of the present invention.

Next, a third embodiment of the present invention will be described with reference to FIG. 16. FIG. 16 illustrates a configuration of an endoscope apparatus 1D of the third embodiment of the present invention. The endoscope apparatus 1A of the first embodiment is a narrow band observation endoscope apparatus that makes an endoscope observation using narrow band illumination light.

By contrast, the endoscope apparatus 1D of the present embodiment is a fluorescence observation endoscope apparatus that makes a fluorescence observation.

The endoscope apparatus 1D has an endoscope 2D for fluorescence observation, a light source section 3D for generating excitation light for fluorescence observation and illumination light for acquiring a reflected light image, a processor 4D that performs signal processing for fluorescence observation and the monitor 5.

The endoscope 2D includes an excitation light cut filter 61 disposed in front of the CCD 11 in the endoscope A of the first embodiment.

As the CCD 11, a CCD with high sensitivity which is a CCD device itself provided with a signal multiplier function may be used.

The light source section 3D of the present embodiment corresponds to the light source section 3A of the first embodiment with the revolving filter 25 mounted with a filter 6Re that allows to pass a predetermined wavelength band to obtain a reflected light image and two excitation light filters 6E1 and 6E2 (see FIG. 17) having transmission characteristics (see FIG. 18) of generating excitation light of the same wavelength band to acquire a fluorescence image instead of the narrow band G, B filters 6G, 6B1 and 6B2.

Figure 17:
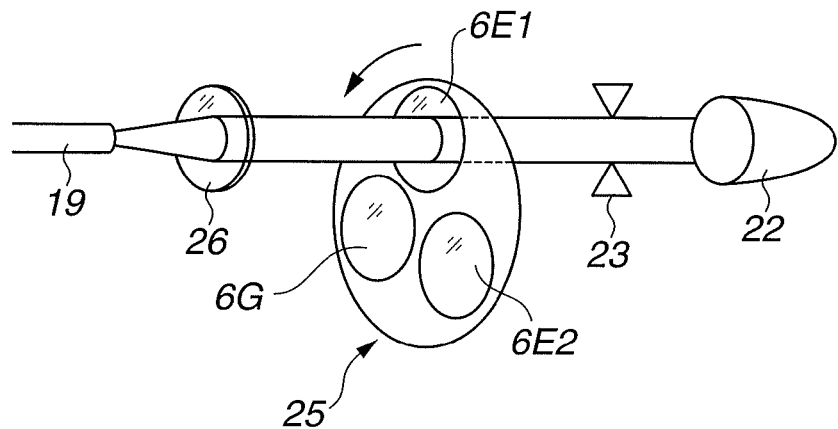
FIG. 17 is a diagram illustrating a configuration of the revolving filter peripheral section of the light source section of the third embodiment.

FIG. 17 illustrates a configuration of a peripheral section of the revolving filter 25 of the light source section 3D. As for the excitation light filters 6E1 and 6E2, the example of transmittance characteristics shown in FIG. 18 illustrates an example where the wavelength band of B is allowed to pass, but the excitation light filters are not limited to this wavelength band, and any filters that allow to pass a wavelength band in which a fluorescence wavelength to be observed can be efficiently generated may be adopted.

Furthermore, the filter 6Re for obtaining a reflected light image may be one that allows to pass any one of, for example, wide wavelength bands R, G and B. Furthermore, the filter 6Re is not limited to a wideband one, but may be one having narrow band transmission characteristics. Moreover, the filter 6Re may also be one that allows to pass a near-infrared wavelength band.

Figure 18:
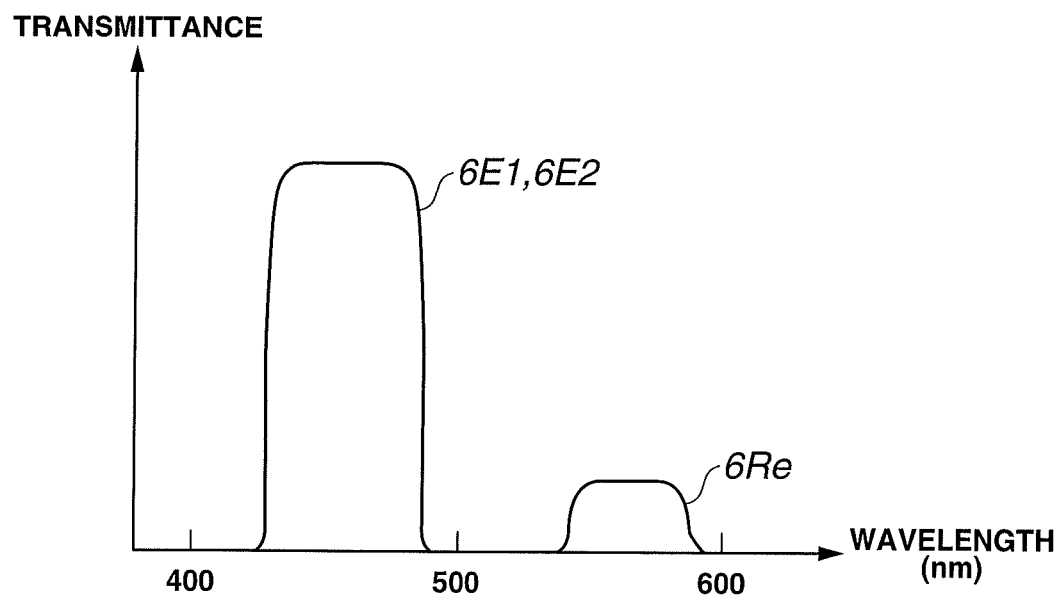
FIG. 18 is a diagram illustrating an example of transmittance characteristics of an excitation light filter and a reflected light filter.

Compared to intensity of normal reflected light, returning light incident upon the CCD 11 side by fluorescent light emission from the region (to be observed) of the subject through radiation of excitation light is very weak, and therefore the present embodiment sets, for example, transmission characteristics of the filters 6E1 and 6E2 that allow to pass the excitation light as shown in FIG. 18 so as to be sufficiently larger than the transmission characteristics of the filter 6Re.

In FIG. 18, the filters 6E1 and 6E2 are set to characteristics that allow to pass, for example, light of a wavelength band of B.

Furthermore, the filter 6Re shown in FIG. 18 is designed to have transmission characteristics of, for example, a wavelength band of G. For this reason, an image pickup signal picked up with the filter 6Re (denoted as "Re" for simplicity) is stored in the first frame memory 34a, then read and becomes an image signal Re via the image processing circuit 35. The image signal Re is inputted to the color conversion circuit 67 together with a fluorescent image signal F, which will be described below. Both image signals Re and F are color-converted to image signals F, Re and F by the color conversion circuit 67 and the image signals F, Re and F are outputted to the R, G and B channels of the monitor 5 respectively via the D/A conversion circuit 36 as shown in FIG. 16.

On the other hand, at the time of radiation of excitation light passing through the excitation light filters 6E1 and 6E2, fluorescence image pickup signals F1 and F2 outputted from the CCD 11 are stored, for example, in the second frame memory 34b and the third frame memory 34c, further read and inputted to the image processing circuit 35.

The image processing circuit 35 performs the same processing as that of reading the image pickup signals G, B1 and B2 of the first embodiment as the image pickup signals Re, F1 and F2 and outputs the image signals Re and F.

In the present embodiment, as in the case of the first embodiment, intensity of the fluorescence image that enters the CCD 11 as fluorescence from the region to be observed is very weak, and therefore the fluorescence picked-up images F1 and F2 obtained by radiating the same excitation light onto the same region twice are subjected to an aligned addition in consideration of an amount of pixel misalignment to generate a fluorescence image as a synthetic image. Therefore, it is possible to generate a fluorescence image with a high S/N (though different from the picked-up image under narrow band illumination light of the first embodiment) and display the fluorescence image as an endoscope image.

Figure 19:
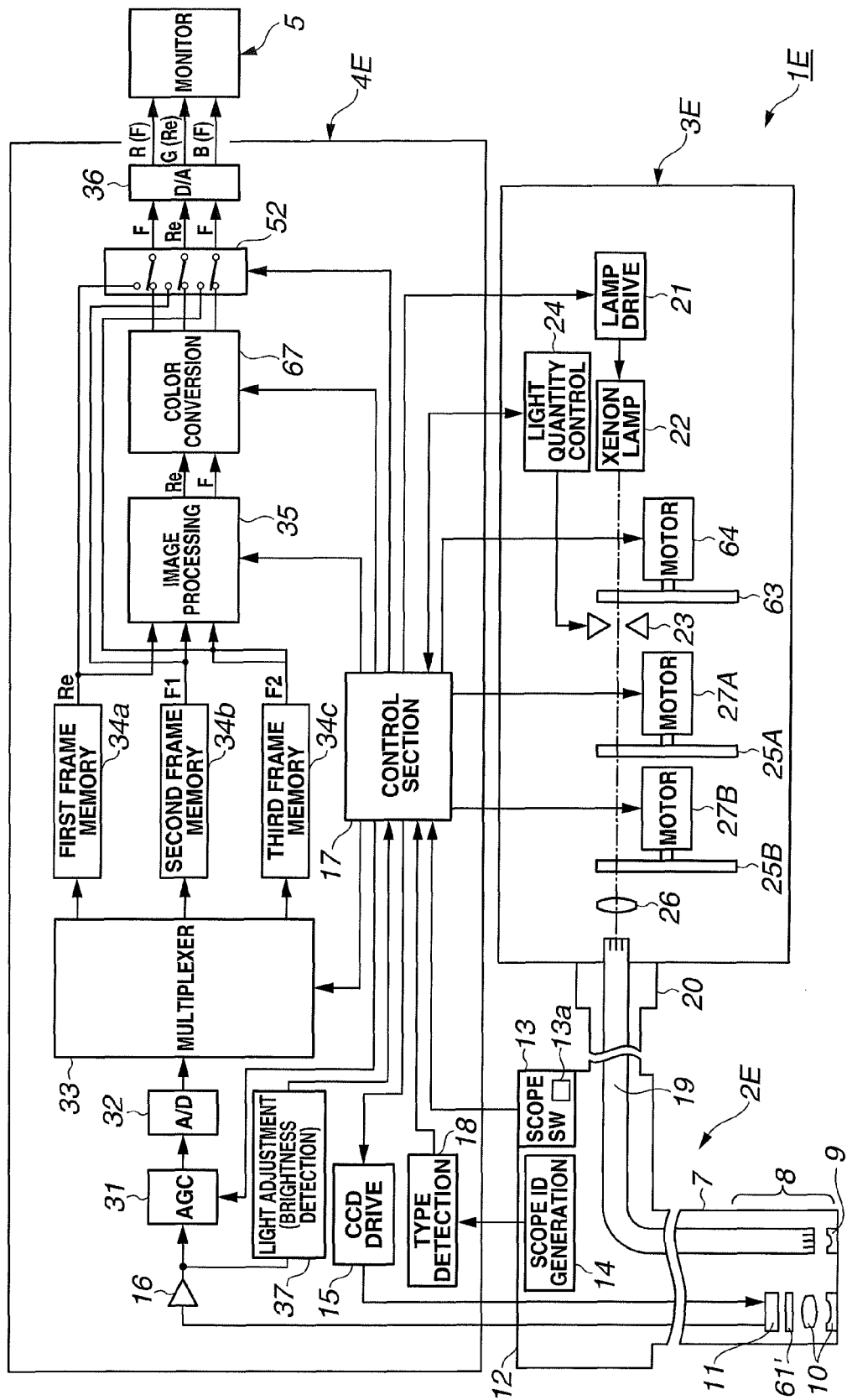
FIG. 19 is a diagram illustrating an overall configuration of an endoscope apparatus according to a modification example of the third embodiment of the present invention.

Next, a modification example of the present embodiment will be described with reference to FIG. 19. FIG. 19 illustrates an endoscope apparatus 1E of the modification example. As will be described below, the endoscope apparatus 1E can perform endoscopy in three observation modes.

The endoscope apparatus 1E has an endoscope 2E for normal observation, fluorescence observation and NBI observation, a light source section 3E for generating illumination light for normal observation, fluorescence observation and NBI observation, a processor 4E and the monitor 5.

The endoscope 2E corresponds to the endoscope 2D in FIG. 16 with the scope switch 13 further provided with an observation mode changeover switch 13a that switches between observation modes.

The control section 17 controls the light source section 3E and the processor 4E according to the operation of the observation mode changeover switch 13a.

The light source section 3E corresponds to the light source section 3D in FIG. 16 including two revolving filters 25A and 25B driven to rotate in synchronization with each other as in the case of the light source section 3C in FIG. 13 or FIG. 14A and FIG. 14B instead of one revolving filter 25, and is further provided with an option filter 63 having optical characteristics different from those of the option filter 51 in FIG. 13.

Furthermore, the option filter 63 selects and sets a filter to be disposed on the optical path through rotation at a predetermined angle by the motor 64 under the control of the control section 17.

Figure 20:
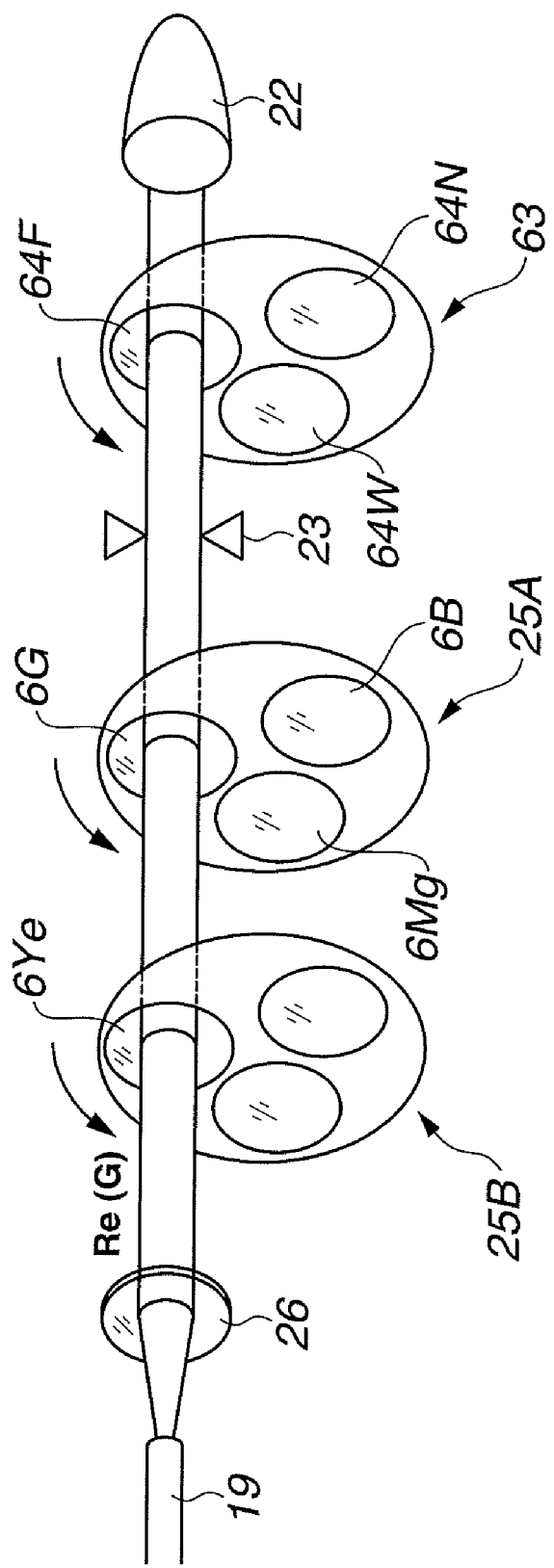
FIG. 20 is a diagram illustrating a configuration of the revolving filter peripheral section of the light source section.

FIG. 20 illustrates the revolving filter peripheral section in the light source section 3E. As described above, the revolving filter 25A is mounted with filters 6Mg, 6G and 6B that allow to pass wide wavelength bands of Mg, G and B at three openings provided in the circumferential direction of a disk.

On the other hand, the revolving filter 25B is mounted with a filter 6Ye that allows to pass a wide wavelength band of Ye only at one of three openings provided in the circumferential direction of a disk.

On the other hand, the option filter 63 is mounted with a fluorescence option filter 64F, an NBI option filter 64N and a normal option filter 64W at three openings provided in the circumferential direction of a disk. FIG. 20 illustrates the fluorescence option filter 64F disposed on the optical path.

Figure 21:
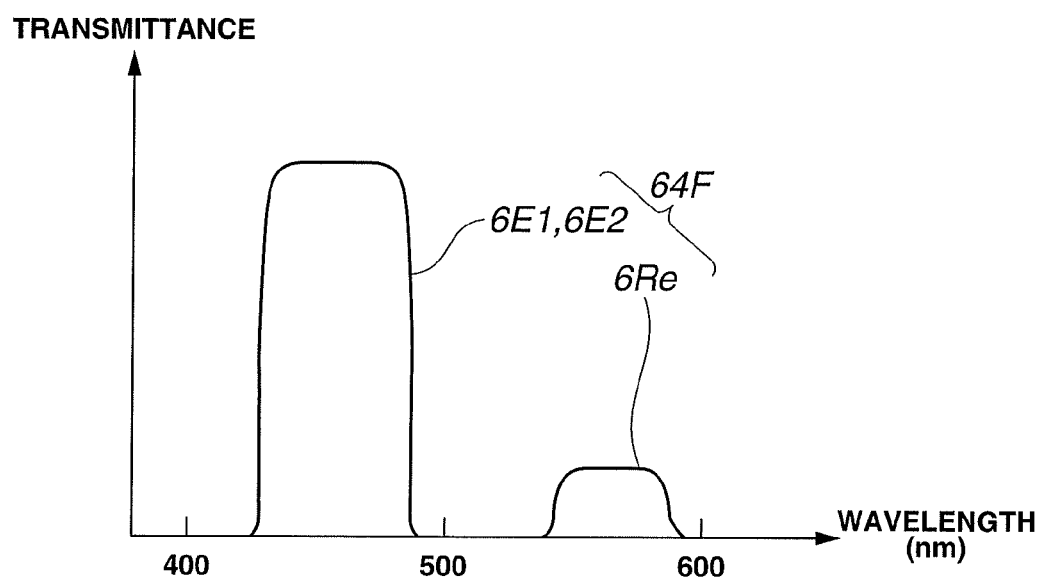
FIG. 21 is a diagram illustrating an example of transmittance characteristics of a fluorescence option filter.

The fluorescence option filter 64F has transmission characteristics including two transmission characteristics of the filters 6Re and 6E1 (or 6E2) shown in FIG. 18. FIG. 21 illustrates an example of transmission characteristics of the fluorescence option filter 64F.

As for the transmission characteristics of the fluorescence option filter 64F as shown in FIG. 21, greater transmittance is set for the wavelength bands (6E1, 6E2) used as excitation light than for the wavelength band (6Re) used as a reflected light image as in the case shown in FIG. 18.

The wavelength band used as excitation light in the fluorescence option filter 64F is set to characteristics that do not allow to pass the narrow wavelength band of B of the NBI option filter 64N (wavelength band shown with the filters 6B1 and 6B2 in FIG. 3A).

Furthermore, the excitation light cut filter 61 disposed in front of the CCD 11 cuts only the wavelength band of the excitation light component in FIG. 21 (that is, wavelength bands shown with 6E1 and 6E2) and has characteristics that allow to pass the narrow wavelength band of B of the NBI option filter 64N in that case.

The normal option filter 64W has transmission characteristics transparent to wide wavelength bands of R, G and B, namely, the visible region.

Furthermore, the NBI option filter 64N has transmission characteristics including the transmission characteristics of both filters 6G and 6B1 (or 6B2) shown in FIG. 3A.

Furthermore, the processor 4E has the same configuration as that of the processor 4C shown in FIG. 13 except that the color conversion circuit 67 is provided between the image processing circuit 35 and the changeover switch 52. However, while the processor 4C in FIG. 13 is used in the normal observation mode and the NBI observation mode, the processor 4E in the present modification example is further used in the fluorescence observation mode, too.

In the processor 4E, the control section 17 selects the changeover switch 52 in the normal observation mode so that the image processing circuit 35 is bypassed as in the case of the processor 4C.

By contrast, in the NBI observation mode and the fluorescence observation mode, the control section 17 selects the changeover switch 52 so that the respective image pickup signals are inputted to the image processing circuit 35. For example, in the fluorescence observation mode, image pickup signals Re, F1 and F2 are inputted to the image processing circuit 35 as shown in FIG. 19.

The image pickup signals are then subjected to image processing as described in FIG. 16, image signals Re and F outputted from the image processing circuit 35 are converted to image signals F, Re and F by the color conversion circuit 67 and then outputted to the R, G and B channels of the monitor 5 via the changeover switch 52 and the D/A conversion circuit 36.

On the other hand, in the NBI observation mode, the image pickup signals are processed in the same way as in the first embodiment.

Therefore, the present modification example has not only the effects of the third embodiment but also the effects of the first embodiment and the effect of being able to make a normal observation.

Fourth Embodiment

Figure 22:
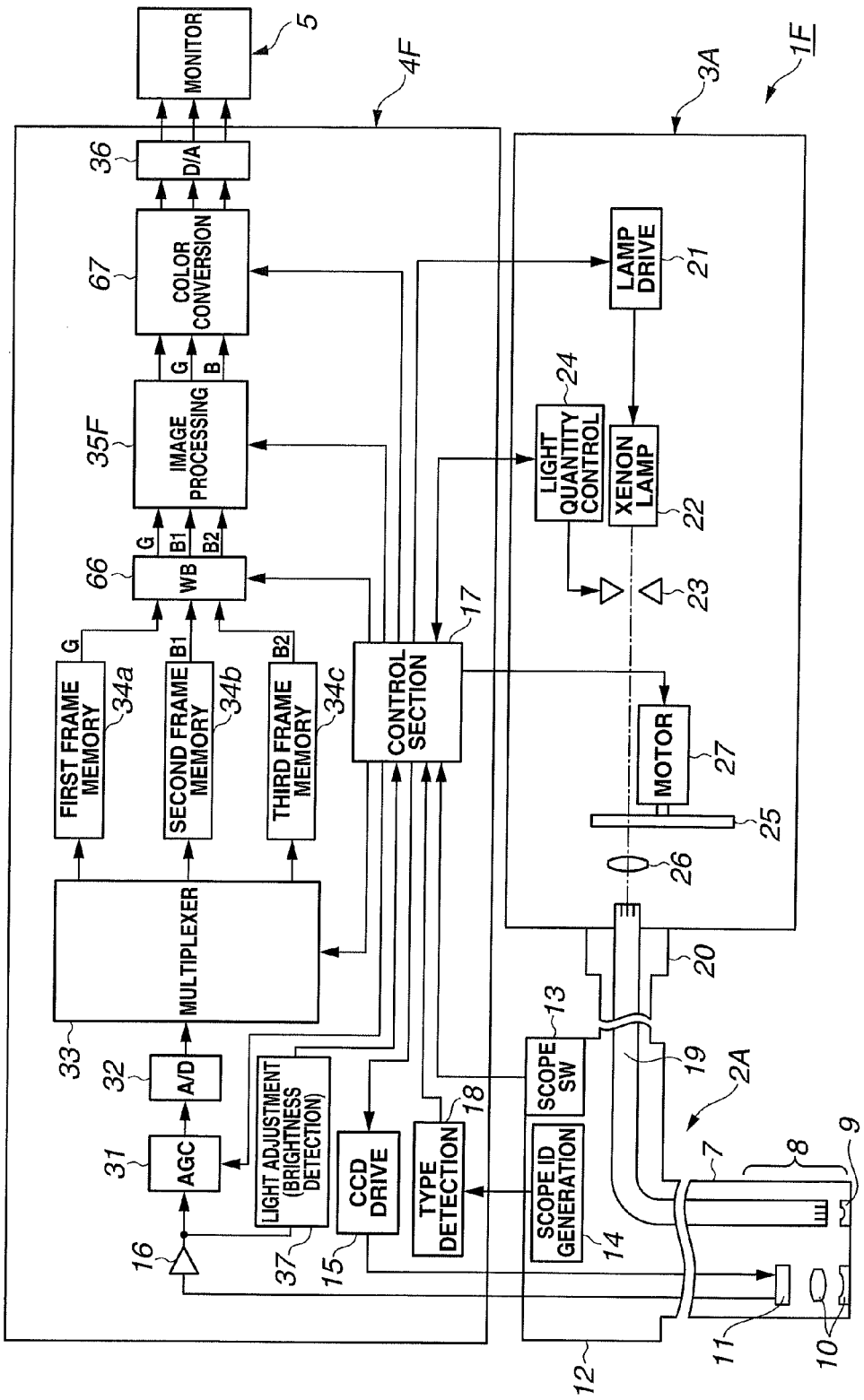
FIG. 22 is a diagram illustrating an overall configuration of an endoscope apparatus according to a fourth embodiment of the present invention.

Next, a fourth embodiment of the present invention will be described with reference to FIG. 22. FIG. 22 illustrates an endoscope apparatus 1F of the fourth embodiment of the present invention. The endoscope apparatus 1F of the present embodiment uses a processor 4F that adopts an image processing circuit 35F which performs image processing different from that of, for example, the image processing circuit 35 of the endoscope apparatus 1A of the first embodiment.

A white balance adjustment circuit (abbreviated as "WB adjustment circuit") 66 is provided on the input side of the image processing circuit 35F. The white balance adjustment circuit is abbreviated as "WB" in the figure.

Under the control of the control section 17, the WB adjustment circuit 66 adjusts image pickup signals B1 and B2 by multiplying the signals by WB adjustment coefficients W1 and W2 and outputs the signals as WB-adjusted image pickup signals B1 and B2 to the subsequent stage. The WB adjustment coefficients W1 and W2 in this case are W1=G detection/(k×B1 detection) and W2=G detection/(k×B2 detection).

Here, k denotes a predetermined value (e.g., 2) and is the same as the value k described in the first embodiment. Furthermore, for example, "G detection" represents an accumulation value of detection signal that has detected an image pickup signal G. The coefficient of the image pickup signal G is not adjusted as a reference (coefficient thereof=1) for WB adjustment.

The image processing circuit 35F performs image processing of alignment between the image pickup signals B1 and B2 picked up in the same wavelength band of the inputted image pickup signals G, B1 and B2.

Furthermore, the image signals G and B outputted from the image processing circuit 35F are color-converted by the color conversion circuit 67 and outputted to the monitor 5 via the D/A conversion circuit 36. The color conversion circuit 67 color-converts the inputted image signals G and B according to following Equation 5. Hereinafter, converted image signals are also expressed in abbreviated form using R, G and B.

[Equation 5]

$$\begin{bmatrix} R \\ G \\ B \end{bmatrix} = Mat4 \begin{bmatrix} G \\ B \end{bmatrix} \quad Mat4 = \begin{bmatrix} m & 0 \\ 0 & n1 \\ 0 & n2 \end{bmatrix} \quad (5)$$

m, n1, n2: predetermined value

In addition to the color conversion circuit 67, a circuit for performing magnification or interpolation or a circuit for performing contour enhancement or the like may be provided. The color conversion circuit 67 or the like may be provided for the other embodiments likewise.

Figure 23:
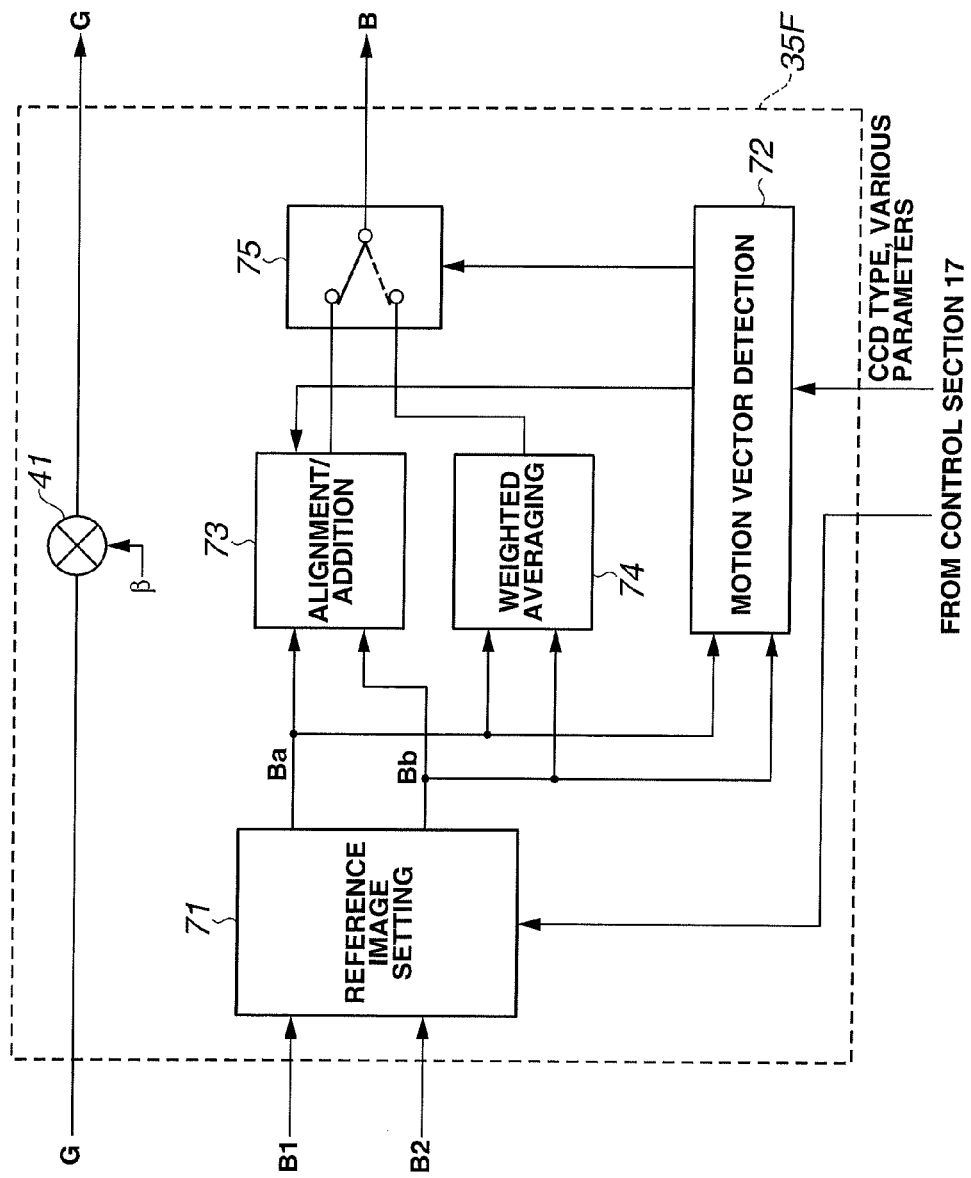
FIG. 23 is a block diagram illustrating a configuration of the image processing circuit.

FIG. 23 illustrates a configuration of the image processing circuit 35F. The image processing circuit 35F includes a reference picked-up image setting circuit (abbreviated as "reference image setting circuit") 71 that sets a reference picked-up image from picked-up images of the inputted image pickup signals B1 and B2 (hereinafter, abbreviated as "picked-up images B1 and B2"), a motion vector detection circuit 72 that detects a motion vector from the set picked-up image, an aligned addition circuit 73 that aligns between the picked-up images and adds up the picked-up images as a synthetic image generation section, a weighted averaging circuit 74 that performs weighted averaging as an alternate image generation section and a switching circuit 75 that switches between output signals of the aligned addition circuit 73 and the weighted averaging circuit 74 and outputs the selected output signal.

The picked-up image of the image pickup signal G is outputted as an image signal G multiplied β-fold by the image processing circuit 35F as in the case of the first embodiment.

In the first embodiment, the determination circuit 42 that forms an amount of misalignment detection section calculates cross-correlation between both picked-up images within both local regions set beforehand between the two picked-up images and detects an amount of misalignment based on a comparison between a maximum value of the normalized cross-correlation and a threshold.

By contrast, the motion vector detection circuit 72 that serves as a motion vector detection section according to the present embodiment detects an amount of misalignment which corresponds to a maximum cross-correlation as a motion vector between the blocks. When motion vectors match each other among at least a predetermined number of blocks, the motion vector detection circuit 72 performs alignment using the motion vector as a motion vector between the picked-up images.

Under the control section 17, the reference image setting circuit 71 sets a picked-up image closer in image pickup timing to the picked-up image G between both picked-up images B1 and B2 as the picked-up image to be a reference for alignment.

Hereinafter, with regard to the picked-up image G, suppose one picked-up image Bb which has closer image pickup timing between the picked-up images B1 and B2 is a reference image and the other picked-up image Ba is an aligned image (that is, an aligned image which becomes the aligned side).

The control section 17 inputs information on the type of the CCD 11 used to generate a picked-up image and various parameters or the like to the motion vector detection circuit 72. The motion vector detection circuit 72 performs processing by changing processing parameters used to detect a motion vector corresponding to the inputted information.

The motion vector detection circuit 72 outputs the detected motion vector as an amount of alignment (amount of misalignment) to the aligned addition circuit 73 when an aligned addition is performed.

Furthermore, when the motion vector detection circuit 72 cannot detect any motion vector, the motion vector detection circuit 72 selects a picked-up image subjected to weighted averaging by the weighted averaging circuit 74 as an alternate image generation section and controls the switching (selection) of the switching circuit 75 so that the image processing circuit 35F outputs the picked-up image as the processing image B subjected to image processing.

The motion vector detection circuit 72 may output the detection result to the control section 17 and the control section 17 may control the switching circuit 75 to perform switching. Furthermore, in the present embodiment, the motion vector detection circuit 72 operates under the control of the control section 17, but in addition to the control section 17, the image processing circuit 35F may also be configured to include a control circuit that controls the motion vector detection circuit 72.

Furthermore, the configuration shown in FIG. 23 is such a configuration that both images Ba and Bb are inputted in parallel to the aligned addition circuit 73 and the weighted averaging circuit 74, but the present invention is not limited thereto. For example, one of the aligned addition circuit 73 and the weighted averaging circuit 74 may be selectively generated according to the motion vector detection result of the motion vector detection circuit 72 or the processing image B generated through the selective processing may be outputted from the image processing circuit 35F. The rest of the configuration is the same as that of the first embodiment.

Next, the operation of mainly the motion vector detection circuit 72 in the image processing circuit 35F according to the present embodiment will be described with reference to the flowchart in FIG. 24.

When the operation of the image processing circuit 35F starts, in first step S41, the motion vector detection circuit 72 generates reduced images Ba' and Bb' from the aligned image Ba and the reference image Bb at a reduction ratio corresponding to the type of the number of pixels of the CCD 11 under the control of the control section 17.

The aligned image Ba and the reference image Bb are reduced at a reduction ratio of 1/3 when, for example, the number of pixels of the CCD 11 is large, 1/2 when the number of pixels is medium and 1 when the number of pixels is small.

To be more specific, processing of thinning the original image (of the aligned image Ba and the reference image Bb) is performed according to the reduction ratio.

Through the processing in step S41, the aligned reduced image Ba' and the reference reduced image Bb' reduced according to the reduction ratio are generated.

In next step S42, the motion vector detection circuit 72 performs block division processing of dividing the reduced images Ba' and Bb' into a plurality of blocks under the control of the control section 17.

In this case, the start coordinates, block size, (maximum) amount of alignment movement (dh_max, dv_max), the number of horizontal and vertical blocks (H, V) are inputted as control information when block division from the control section 17 is performed.

In the present embodiment, the number of blocks (H, V) is fixed, for example, to (3, 3). Of course, the present invention is not limited to this case. Furthermore, the amount of alignment movement (dh_max, dv_max) corresponds to the range (region) in which the motion vector is detected and is used in the processing in step S48 which will be described later.

The motion vector detection circuit 72 then generates block images of a plurality of (nine) blocks into which the reduced images Ba' and Bb' are each divided into three portions horizontally and vertically.

As shown in next step S43, the motion vector detection circuit 72 performs processing of calculating brightness in each block, that is, calculating brightness of a block image.

That is, in step S43, the motion vector detection circuit 72 calculates a brightness average value or an accumulation value of brightness of each pixel for each block in the reduced images Ba' and Bb'.

Furthermore, in step S44, the motion vector detection circuit 72 performs processing of edge extraction on the block image.

For this reason, the motion vector detection circuit 72 uses horizontal (H) direction (3×3) and vertical (V) direction (3×3) differential filters as extraction operators (extraction operators) for performing edge extraction.

The motion vector detection circuit 72 adds up the absolute values of extraction data extracted at each pixel (each position) through the extraction operators in H and V directions separately.

In next step S45, the motion vector detection circuit 72 performs processing of calculating edge intensity. In this case, processing of calculating an average value or accumulation value of edge intensity in the block is performed.

In next step S46, the motion vector detection circuit 72 performs (motion vector detection) block selection processing from information on brightness per block calculated through the processing of calculating brightness in the block in step S43 and information on edge intensity per block calculated through the processing of calculating edge intensity in the block in step S45.

The block selection processing selects bright or prominent edge blocks, reduces the number of blocks and thereby reduces the amount of calculation of motion vector (derivation of cross-correlation in particular) as will be described later.

To be more specific, the motion vector detection circuit 72 excludes a predetermined number of dark blocks from motion vector processing target blocks in descending order of darkness. Furthermore, the motion vector detection circuit 72 excludes a predetermined number of blocks from motion vector processing target blocks in ascending order of edge intensity.

Thus, using information on brightness and information on edge intensity, the motion vector detection circuit 72 designates 2/3 of all blocks (here, nine blocks) as blocks to be excluded from processing targets and the remaining blocks as blocks selected to be processed.

The motion vector detection circuit 72 then assigns an ID (identification information) to the selected block and moves to the next processing. In next step S47, the motion vector detection circuit 72 binarizes the edges of the selected block assigned the ID in the reduced images Ba' and Bb' whose edge intensity is calculated through the processing of edge intensity calculation and performs processing of edge binarization (within the selected block) to generate a binarized edge image.

The threshold used for binarization is adjusted for each selected block through a calculation of (predetermined threshold)×(brightness average of selected block)/(predetermined brightness average). The above described brightness average may be an accumulation value of brightness of each pixel.

In next step S48, the motion vector detection circuit 72 performs processing of cross-correlation derivation on the above described binarized edge image.

To be more specific, the motion vector detection circuit 72 moves one binarized edge image within the amount of alignment movement (dh_max, dv_max) for each block for which the corresponding binarized edge image is calculated in both reduced images Ba' and Bb' and calculates a cross-correlation cv at each position between the one binarized image and the other binarized image.

In this case, the cross-correlation cv is expressed as:

$$cv(dh,dv)=\Sigma Bb'(h,v)*Ba'(h+dh,v+dv) \qquad (6)$$

Here, $\Sigma$ denotes a sum total obtained by multiplying the pixel Bb'(h, v) value of the reduced image Bb' in the horizontal and vertical positions (h, v) within the block (to be processed) by the pixel Ba'(h+dh, v+dv) value of the reduced image Ba' in the horizontal and vertical positions (h+dh, v+dv) moved from the horizontal and vertical positions (h, v) thereof to the horizontal and vertical positions by the amount of alignment movement (dh, dv) and adding up the multiplication values at all positions h and v within the block. In this case, dh≦dh_max, dv≦dv_max.

Furthermore, the motion vector detection circuit 72 derives a maximum value at which the cross-correlation cv becomes a maximum within the amount of alignment movement (dh_max, dv_max). Furthermore, the motion vector detection circuit 72 sets the amount of movement at which the cross-correlation cv reaches a maximum value as a motion vector. The motion vector detection circuit 72 then derives a motion vector for each selected block.

In next step S49, the motion vector detection circuit 72 performs motion vector determining processing of determining whether or not each motion vector derived for each selected block in step S48 is a motion vector appropriate for alignment of all picked-up images.

To be more specific, in step S48, the motion vector detection circuit 72 checks whether or not each motion vector derived for each selected block matches each other among different blocks, or the degree of match.

In this case, if the motion vectors match each other among at least the majority of blocks, the motion vector detection circuit 72 determines that the motion vectors (considered to be appropriate) have been successfully detected and designates those that match each other among at least the majority of blocks as the motion vectors. Furthermore, in this case, the motion vectors are outputted.

The horizontal component and the vertical component of the motion vector are abbreviated as "dh" and "dv" (to be more exact, expressed as "specific dh" and "specific dv") and represented as motion vector (dh, dv).

By contrast, when the motion vectors match each other among only fewer than the majority of blocks, the motion vector detection circuit 72 determines that it is not possible to detect the motion vectors.

As shown in step S50, the motion vector detection circuit 72 controls processing of aligned addition by the aligned addition circuit 73 or weighted averaging by the weighted averaging circuit 74 using the information on whether or not the motion vectors can be detected.

Figure 25:
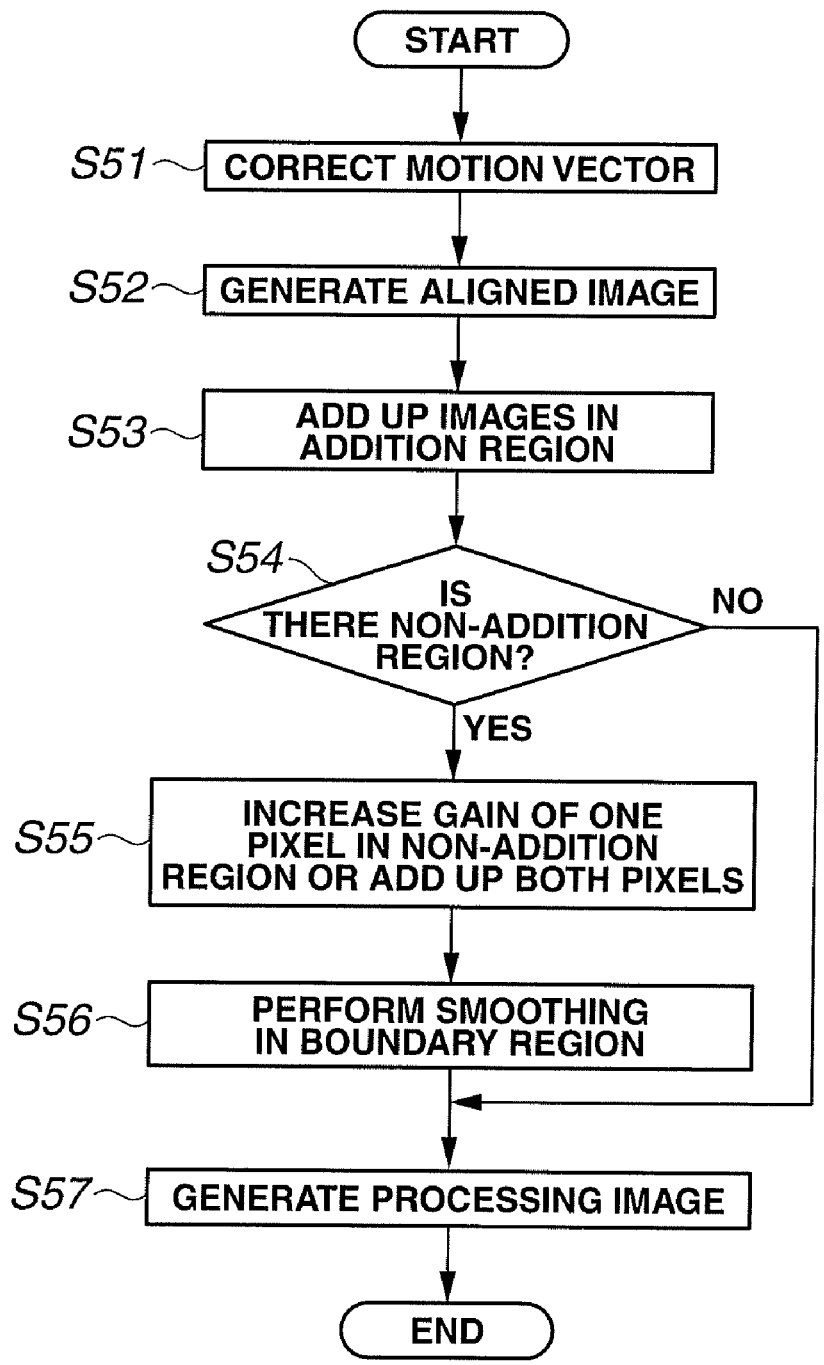
FIG. 25 is a flowchart illustrating processing contents of an aligned addition.

Next, the processing by the aligned addition circuit 73 when the motion vector detection circuit 72 detects a motion vector will be described. FIG. 25 illustrates processing contents by the aligned addition circuit 73 when a motion vector is detected.

In first step S51, for example, the aligned addition circuit 73 performs motion vector correction processing. The motion vector detection circuit 72 may perform the motion vector correction processing and output the corrected motion vector to the aligned addition circuit 73.

Figure 24:
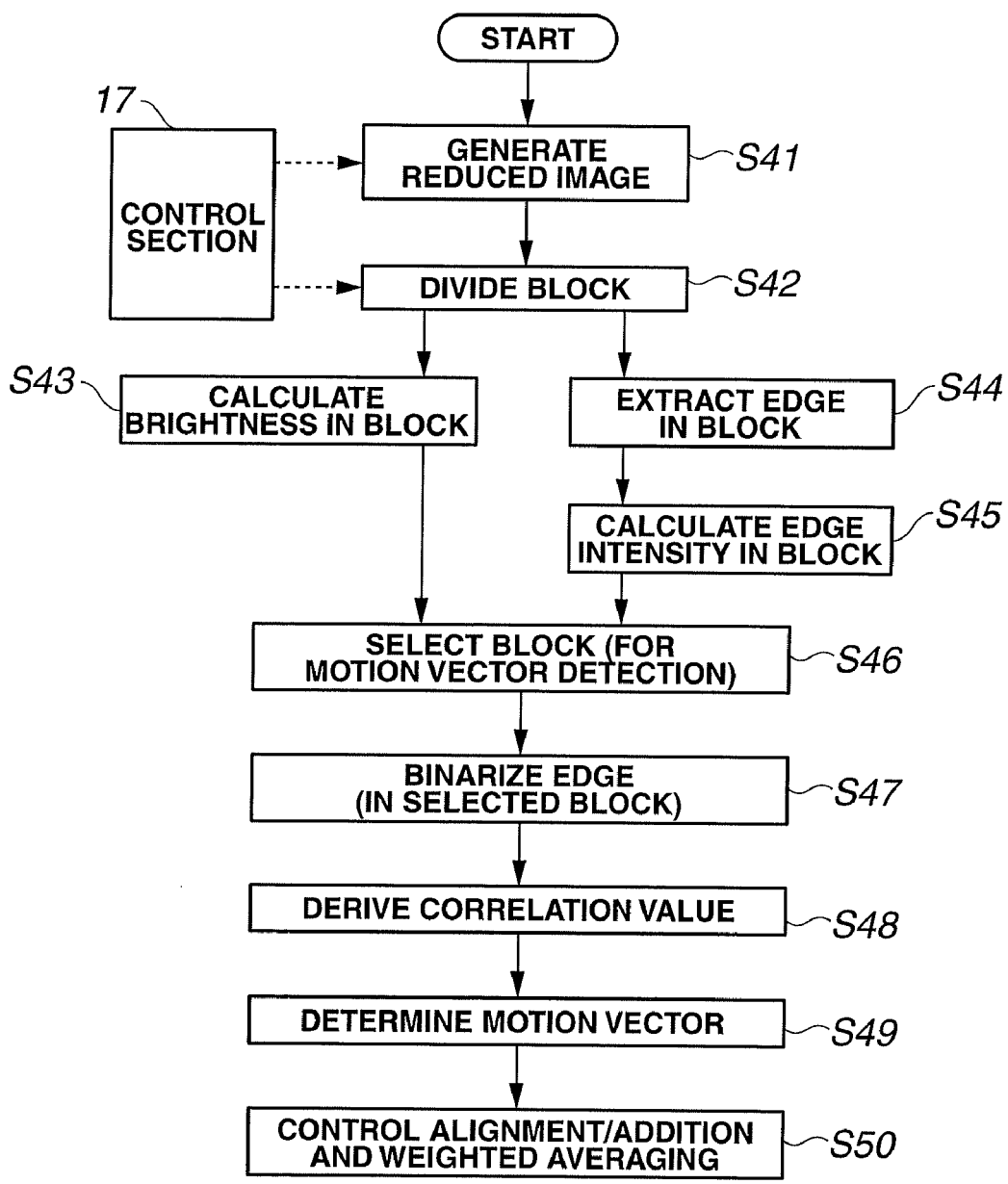
FIG. 24 is a flowchart illustrating operation of the image processing circuit according to the fourth embodiment.

To be more specific, since the motion vector (dh, dv) calculated in step S49 of FIG. 24 corresponds to (one of) the reduced images Ba' and Bb', the motion vector is corrected to the motion vector corresponding to the non-reduced original image, that is, the corrected motion vector.

To be more specific, assuming the aforementioned reduction ratio is s, the horizontal component dh and the vertical component dv in the motion vector (dh, dv) are divided by the reduction ratio s respectively and the corrected motion vector (dh', dv') is calculated.

In next step S52, the aligned addition circuit 73 performs processing of generating an aligned image Ba".

To be more specific, the aligned addition circuit 73 moves each pixel of the inputted aligned image Ba by the corrected motion vector (dh', dv') calculated in preceding step S51 and generates the aligned image Ba".

In next step S53, the aligned addition circuit 73 performs image addition processing between the reference image Bb and the aligned image Ba" in a region where the corresponding pixels exist (also referred to as "addition region").

To be more specific, the aligned addition circuit 73 adds up the reference image Bb and the aligned image Ba" generated in step S52 and generates pixel B(h, v) at each position (h, v) of the added processing image B. In this case, the pixel B(h, v) is generated by:

$$B(h,v)=\alpha \times Ba''(h,v)+Bb(h,v) \qquad (7)$$

where $\alpha$ is the same as that of the first embodiment.

In next step S54, the aligned addition circuit 73 determines whether or not there is a region where the corresponding pixels do not exist (also referred to as "non-addition region") between both images Bb and Ba" described above. When the non-addition region exists, in next step S55, the aligned addition circuit 73 performs processing in the non-addition region.

To be more specific, when an attempt to perform the processing in Equation 7 is made in the non-addition region, since the pixel Ba"(h, v) corresponding to each pixel Bb (h, v) of the reference image Bb does not exist, the gain of each pixel Bb(h, v) is increased (the gain is multiplied $\alpha$-fold) or the specific pixel Bb(h, v) is multiplied $\alpha$-fold and the pixels are added up.

In addition, both pixels may be added up, that is, $\alpha \times Ba(h, v)+Bb(h, v)$ may be calculated and designated as a pixel B(h, v) in the non-converted region.

Furthermore, as shown in step S56, smoothing processing is performed using a low pass filter or the like in the boundary region between the addition region and the non-addition region.

In next step S57, the aligned addition circuit 73 generates a processing image B of the image processing circuit 35F through the image addition in the addition region in step S53, the processing in the non-addition region in step S55 and the processing in the boundary region in S56, and outputs the processing image B from the image processing circuit 35F.

On the other hand, in step S54, when the non-addition region does not exist, the image generated in step S53 is designated as the processing image in step S57.

When the result of the motion vector determining processing in step S49 in FIG. 24 shows that it is not possible to detect the motion vector, the weighted averaging circuit 74 performs weighted averaging on both images Ba and Bb, and a processing image is generated through the weighted averaging and outputted from the image processing circuit 35F.

In this case, as the weighted average, a weighted average may be adopted, which is calculated as follows using, for example, coefficient δ (0≦δ≦1, for example, δ=0.5):

$$B(h,v)=\alpha\times\{(1-\delta)\times Ba(h,v)+\delta\times Bb(h,v)\}+Bb(h,v) \quad (8)$$

When it is not possible to detect an appropriate motion vector, the processing image displayed as an endoscope image is generated by calculating the above described weighted average without using the motion vector, and therefore it is possible to secure certain image quality and generate a processing image. Namely, even if the appropriate motion vector cannot be detected, if alignment is performed using the motion vector, it is difficult to secure certain image quality through the motion vector.

Thus, the present embodiment radiates the same region twice with light of the same wavelength band, picks up images with returning light from the same region and the image processing circuit 35F detects a motion vector corresponding to the amount of misalignment between the corresponding pixels between both picked-up images of both image pickup signals from the two image pickup signals.

When the appropriate motion vector can be detected, one picked-up image is shifted and the picked-up images are added up, and it is thereby possible to generate an image with a better S/N than when only one picked-up image is used.

Furthermore, when the appropriate motion vector cannot be detected, images are generated by calculating a weighted average without using the motion vector, and it is thereby possible to generate an image keeping certain image quality.

In the fourth embodiment, for example, the image processing circuit 35F performs image processing of detecting a motion vector on an image pickup signal that has passed through the AGC circuit 31, but the image processing circuit 35F may also perform image processing of detecting a motion vector on an image pickup signal before passing through the AGC circuit 31 and then pass the image pickup signal through the AGC circuit 31 and perform AGC gain control. The same will also apply to embodiments or the like other than the fourth embodiment.

Furthermore, in the case of a configuration with the AGC circuit 31 provided before the image processing circuit 35F, for example, control may be exerted such that the control section 17 fixes the AGC gain of the AGC circuit 31 and the image processing circuit 35F performs image processing of detecting a motion vector.

Furthermore, the image processing circuit 35F described in the present embodiment may also be applied to other embodiments or modification examples or the like.

Embodiments or the like configured by partially combining the aforementioned embodiments also belong to the present invention.

What is claimed is:

1. An image pickup apparatus, comprising:
a light source section that can radiate at least two light beams of the same wavelength onto the same region of a subject at different timings within a one-frame period making up one image;
a brightness detection section that detects brightness of two returning light images based on the radiation of the at least two light beams of the same wavelength;
an amount-of-misalignment detection section that detects an amount of pixel misalignment between the at least two returning light images;
a determining section that determines whether or not to generate a synthetic image based on the detection result of the amount-of-misalignment detection section when the detection result of the brightness detection section is darker than a target brightness; and
a synthetic image generation section that generates the synthetic image obtained by synthesizing the two returning light images using the light beams of the same wavelength and under substantially the same exposure quantity based on the determination result of the determining section.

2. The image pickup apparatus according to claim 1, wherein the amount-of-misalignment detection section shifts a pixel of one of the two returning light images, detects an amount of misalignment of the pixel in the case of a maximum value where a correlation value with the other pixel reaches a maximum,
the determining section determines whether or not to generate the synthetic image or an alternate image based on whether or not the maximum value exceeds a predetermined threshold, and
when the maximum value is determined to exceed the predetermined threshold, the synthetic image generation section shifts pixels by the amount of misalignment of the pixel in the case of the maximum value and adds up the pixels and thereby generates the synthetic image.

3. The image pickup apparatus according to claim 2, wherein a normalized correlation value corrected based on signal intensity of each pixel is used as the correlation value.

4. The image pickup apparatus according to claim 2, further comprising an alternate image generation section that generates an image obtained by multiplying one of the two returning light images by a gain value exceeding 1 as the alternate image,
wherein when the maximum value is determined to be equal to or below the predetermined threshold, the alternate image generation section generates the alternate image.

5. The image pickup apparatus according to claim 1, wherein the light source section can radiate light of a wavelength different from the at least two light beams of the same wavelength, and
comprises an output section that multiplies a returning light image based on radiation of the light of the different wavelength by a gain value based on the detection result of the brightness detection section and outputs the multiplication result.

6. An image pickup apparatus, comprising:
a light source section that can radiate at least two light beams of the same wavelength onto the same region of a subject at different timings within a one-frame period making up one image;
a light quantity adjusting section provided in the light source section for adjusting a light quantity from the light source;
a brightness detection section that detects brightness of two returning light images based on the radiation of the at least two light beams of the same wavelength;
a synthetic image generation section that generates a synthetic image obtained by synthesizing the two returning light images using the light beams of the same wavelength and under substantially the same exposure quantity based on the adjustment result of the light quantity adjusting section and the detection result of the brightness detection section;
an auto gain adjusting section that performs auto gain adjustment so that an image signal corresponding to the synthetic image generated by the synthetic image generation section has a predetermined amplitude; and a control section that controls the light quantity adjusting section, the synthetic image generation section and the auto gain adjusting section, so as to realize a target brightness in descending order of priority of light quantity adjustment by the light quantity adjusting section, adjustment of the amount of addition between the two returning light images by the synthetic image generation section and auto gain adjustment by the auto gain adjusting section, when the brightness detection result of the brightness detection section is darker than the target brightness.

7. The image pickup apparatus according to claim 6, further comprising:
   an amount-of-misalignment detection section that detects an amount of pixel misalignment between at least two returning light images from light of the same wavelength; and
   a determining section that determines whether or not to generate the synthetic image or an alternate image that substitutes for the synthetic image based on the detection result of the amount-of-misalignment detection section.

8. The image pickup apparatus according to claim 6, further comprising:
   a motion vector detection section that divides the two returning light images from the light of the same wavelength into a plurality of blocks respectively and detects a motion vector between the returning light images corresponding to the plurality of divided blocks; and
   a determining section that determines whether or not to generate the synthetic image based on the detection result of the motion vector detection section.

9. The image pickup apparatus according to claim 6, further comprising:
   an amount-of-misalignment detection section that detects an amount of pixel misalignment between at least two returning light images from light of the same wavelength;
   a determining section that determines whether or not to generate the synthetic image or an alternate image that substitutes for the synthetic image based on the detection result of the amount-of-misalignment detection section; and
   an alternate image generation section that generates an image obtained by multiplying one of the two returning light images by a first value or a weighted average image obtained by weighted-averaging the two returning light images and multiplying the weighted average image by a second value as the alternate image;
   wherein when control is performed so as to achieve the target brightness according to the brightness detection result of the brightness detection section, if the alternate image generation section generates the alternate image according to the determination result of the determining section, brightness of the alternate image is adjusted by the first value or the second value.

10. The image pickup apparatus according to claim 6, wherein the brightness detection section detects brightness of two returning light images of the same wavelength reflected on the same region of the subject based on the radiation of the at least two light beams of the same wavelength.

11. An image pickup apparatus, comprising:
    a light source section that can radiate at least two light beams of the same wavelength onto the same region of a subject at different timings within a one-frame period making up one image;
    a light quantity adjusting section provided in the light source section for adjusting a light quantity from the light source section;
    a brightness detection section that detects brightness of two returning light images based on the radiation of the at least two light beams of the same wavelength;
    a synthetic image generation section that generates a synthetic image obtained by synthesizing the two returning light images using the light beams of the same wavelength and under substantially the same exposure quantity based on the adjustment result of the light quantity adjusting section and the detection result of the brightness detection section; and
    an auto gain adjusting section that performs auto gain adjustment so that an image signal corresponding to the synthetic image generated by the synthetic image generation section has a predetermined amplitude;
    wherein when the brightness detection result of the brightness detection section is brighter than a target brightness, the auto gain adjusting section, the synthetic image generation section and the light quantity adjusting section are controlled so as to realize the target brightness in descending order of priority of auto gain adjustment by the auto gain adjusting section, adjustment of the amount of addition between the two returning light images by the synthetic image generation section and light quantity adjustment by the light quantity adjusting section.

12. The image pickup apparatus according to claim 11, further comprising:
    an amount-of-misalignment detection section that detects an amount of pixel misalignment between at least two returning light images from light of the same wavelength; and
    a determining section that determines whether or not to generate the synthetic image or an alternate image that substitutes for the synthetic image based on the detection result of the amount-of-misalignment detection section.

13. The image pickup apparatus according to claim 11, further comprising:
    a motion vector detection section that that divides the two returning light images from the light of the same wavelength into a plurality of blocks respectively and detects a motion vector between the returning light images corresponding to the plurality of divided blocks; and
    a determining section that determines whether or not to generate the synthetic image based on the detection result of the motion vector detection section.

14. The image pickup apparatus according to claim 11, further comprising:
    an amount-of-misalignment detection section that detects an amount of pixel misalignment between at least two returning light images from light of the same wavelength;
    a determining section that determines whether or not to generate the synthetic image or an alternate image that substitutes for the synthetic image based on the detection result of the amount-of-misalignment detection section; and
    an alternate image generation section that generates an image obtained by multiplying one of the two returning light images by a first value or a weighted average image obtained by weighted-averaging the two returning light images and multiplying the weighted average image by a second value as the alternate image;

wherein when control is performed so as to achieve the target brightness according to the brightness detection result of the brightness detection section, if the alternate image generation section generates the alternate image according to the determination result of the determining section, brightness of the alternate image is adjusted by the first value or the second value.

15. The image pickup apparatus according to claim 11, wherein the brightness detection section detects brightness of two returning light images of the same wavelength reflected on the same region of the subject based on the radiation of the at least two light beams of the same wavelength.

16. An image pickup apparatus, comprising:
   a light source section that can radiate at least two light beams of the same wavelength onto the same region of a subject at different timings within a one-frame period making up one image;
   a brightness detection section that detects brightness of two returning light images based on the radiation of the at least two light beams of the same wavelength;
   a motion vector detection section that divides the two returning light images from the light of the same wavelength into a plurality of blocks respectively and detects a motion vector between the returning light images corresponding to the plurality of divided blocks;
   a determining section that determines whether or not to generate a synthetic image based on the detection result of the motion vector detection section when the detection result of the brightness detection section is darker than a target brightness; and
   a synthetic image generation section that generates a synthetic image obtained by performing an aligned addition of the two returning light images using the light beams of the same wavelength and under substantially the same exposure quantity based on the determination result of the determining section.

17. The image pickup apparatus according to claim 16, wherein the determining section determines whether or not to generate the synthetic image based on a determination of whether or not the motion vector detected by the motion vector detection section substantially matches each other among at least a predetermined number of blocks, and when the motion vector detected by the motion vector detection section is determined to substantially match each other among at least a predetermined number of blocks, the synthetic image generation section performs an aligned addition using a motion vector that matches each other among at least a predetermined number of blocks and thereby generates the synthetic image.

18. The image pickup apparatus according to claim 17, further comprising an alternate image generation section that generates a weighted average image obtained by weighted-averaging the two returning light images as an alternate image,
   wherein when the determining section determines that the motion vector does not match each other among at least a predetermined number of blocks, the alternate image generation section generates the alternate image.

* * * * *